US008372891B2

(12) United States Patent
Schlenoff

(10) Patent No.: US 8,372,891 B2
(45) Date of Patent: Feb. 12, 2013

(54) POLYMER MECHANICAL DAMPING COMPOSITES AND METHODS OF PRODUCTION

(75) Inventor: Joseph B. Schlenoff, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/606,122

(22) Filed: Sep. 7, 2012

(65) Prior Publication Data

US 2012/0326348 A1 Dec. 27, 2012

Related U.S. Application Data

(60) Division of application No. 13/482,064, filed on May 29, 2012, now Pat. No. 8,283,030, which is a division of application No. 12/399,690, filed on Mar. 6, 2009, now Pat. No. 8,206,822, which is a continuation-in-part of application No. 12/439,647, filed as application No. PCT/US2007/077146 on Aug. 29, 2007, now Pat. No. 8,206,816.

(60) Provisional application No. 60/823,842, filed on Aug. 29, 2006.

(51) Int. Cl.
*C08J 5/20* (2006.01)
*C08K 3/16* (2006.01)
*C08K 3/34* (2006.01)
*B29C 51/00* (2006.01)
*B29C 59/02* (2006.01)

(52) U.S. Cl. .......... 521/27; 524/413; 524/445; 524/500; 264/239; 264/320; 264/331.11

(58) Field of Classification Search .................... 521/27; 524/413, 445, 500; 264/239, 320, 331.11
See application file for complete search history.

(56) References Cited

U.S. PATENT DOCUMENTS

| | | | |
|---|---|---|---|
| 3,276,598 A | 10/1966 | Michaels et al. | |
| 3,546,142 A | 12/1970 | Michaels et al. | |
| 3,558,744 A | 1/1971 | Michaels et al. | |
| 3,565,973 A | 2/1971 | Michaels | |
| 4,539,373 A | 9/1985 | Mani et al. | |
| 6,566,575 B1 | 5/2003 | Stickels et al. | |
| 6,660,367 B1 | 12/2003 | Yang et al. | |
| 6,740,409 B1 | 5/2004 | Granick et al. | |
| 6,905,875 B2 | 6/2005 | Yu et al. | |
| 7,101,947 B2 | 9/2006 | Schlenoff et al. | |
| 7,105,229 B2 | 9/2006 | Anderson | |
| 7,223,327 B2 | 5/2007 | Schlenoff et al. | |
| 7,238,536 B1 | 7/2007 | Schlenoff | |
| 7,387,824 B2 | 6/2008 | Tamagawa et al. | |
| 2004/0265603 A1 | 12/2004 | Schlenoff | |
| 2005/0282925 A1 | 12/2005 | Schlenoff et al. | |
| 2005/0287111 A1 | 12/2005 | Schlenoff et al. | |
| 2006/0051532 A1* | 3/2006 | Tamagawa et al. | 428/32.39 |
| 2006/0065529 A1 | 3/2006 | Schlenoff et al. | |
| 2006/0073333 A1* | 4/2006 | Anderson | 428/402.2 |
| 2007/0259452 A1 | 11/2007 | Schlenoff | |
| 2007/0265174 A1 | 11/2007 | Schlenoff | |

OTHER PUBLICATIONS

Allen, Norman S., "Polymer Photochemistry", Photochemistry, 2007, vol. 36, pp. 232-297.
Biggerstaff et al., "Damping Performance of Cocured Graphite/Epoxy Composite Laminates with Embedded Damping Materials", Journal of Composite Materials, 1999, vol. 33, No. 15, pp. 1457-1469.
Dai et al., "Controlling the Permeability of Multilayered Polyelectrolyte Films through Derivatization, Cross-Linking, and Hydrolysis", Langmuir, 2001, vol. 17, No. 3, pp. 931-937.
Dubas et al., "Swelling and Smoothing of Polyelectrolyte Multilayers by Salt", Langmuir, 2001, vol. 17, pp. 7725-7727.
Graul et al., "Capillaries Modified by Polyelectrolyte Multilayers for Electrophoretic Separations", Analytical Chemistry, 1999, vol. 71, No. 18, pp. 4007/4013.
Holmlin et al., Zwitterionic SAMs that Resist Nonspecific Adsorption of Protein from Aqueous Buffer, Langmuir, 2001, vol. 17, No. 9, pp. 2841-2850.
Iatridis et al., "The Viscoelastic Behavior of the Non-Degenerate Human Lumbar Nucleus Polposus in Shear", J. Biomechanics, 1997, vol. 30., No. 10, pp. 1005-1013.
Iatridis et al., "Shear Mechanical Properties of Human Lumbar Annulus Fibrosus", Journal of Orthopaedic Research, 1999, vol. 17, No. 5, pp. 732-737.
Jaber et al., "Mechanical Properties of Reversibly Cross-Linked Ultrathin Polyelectrolyte Complexes", Journal of American Chemical Society, 2006, vol. 128, pp. 2940-2947.
Kozlovskaya et al., "Hydrogen-Bonded Polymer Capsules Formed by Layer-by-Layer Self-Assembly", Macromolecules, 2003, vol. 36, pp. 8590-8592.
Lim et al., "Microencapsulated Islets as Bioartificial Endocrine Pancreas", Science, New Series, 1980, vol. 210, No. 4472, pp. 908-910.
Losche et al., "Detailed Structure of Molecularly Thin Polyelectrolyte Multilayer Films on Solid Substrates as Revealed by Neutron Reflectometry", Macromolecules, 1998, vol. 31, No. 25, pp. 8893-8906.
Michaels, Alan S., "Polyelectrolyte Complexes", Industrial & Engineering Chemistry, 1965, vol. 57, No. 10, pp. 32-40.
Rosidian et al., "Ionic Self-Assembly of Ultrahard ZrO2/Polymer Nanocomposite Thin Films", Advanced Materials, 1998, vol. 10, No. 14, pp. 1087-1091.
Smets, G., "Photocross-Linkable Polymers", Journal of Macromolecular Science Chemistry, 1984, A21(13 & 14), pp. 1695-1703.
Strehmel, Veronika, "Epoxies: Structures, Photoinduced Cross-Linking, Network Properties, and Applications", Handbook of Photochemistry and Photobiology, 2003, Chapter 1, pp. 1-110. Sui et al., "Phase Separations in pH-Responsive Polyelectrolyte Multilayers: Charge Extrusion versus Charge Expulsion" Langmuir, 2004, vol. 20, No. 14, pp. 6026-6031.
Timpe, Hans-Joachim, "Polymer Photochemistry and Photo-Cross-Linking", Desk Reference of Functional Polymers: Syntheses and Applications, 1997, pp. 273-291.

(Continued)

Primary Examiner — Michael M Bernshteyn
(74) Attorney, Agent, or Firm — Armstrong Teasdale LLP

(57) ABSTRACT

A method of reshaping an article comprising a polyelectrolyte complex, the polyelectrolyte complex comprising an intermolecular blend of a predominantly positively-charged polyelectrolyte and a predominantly negatively charged polyelectrolyte by controlling the salt doping level.

15 Claims, 10 Drawing Sheets

OTHER PUBLICATIONS

Poly(Ethylene Glycol) Chemistry: Biotechnical and Biomedical Applications (Table of Contents only), edited by Milton J. Harris, 1992, Plenum Press, New York, New York, 13 pages.

R. Reese Handbook of Antibiotics (Table of Contents and Preface only), Third Edition, 2000, 3 pages, Lippincott Williams and Wilkins, Philadelphia, Pennsylvania.

International Search Report, PCT/US2007/77146, dated Mar. 7, 2008, 2 pages.

Written Opinion of the International Searching Authority, PCT/US2007/77146, dated Mar. 7, 2008, 8 pages.

* cited by examiner

POLYMER MECHANICAL DAMPING COMPOSITES AND METHODS OF PRODUCTION

CROSS REFERENCE TO RELATED APPLICATIONS

This application is a divisional application of U.S. application Ser. No. 13/482,064, which was filed May 29, 2012. U.S. application Ser. No. 13/482,064 is a divisional application of U.S. application Ser. No. 12/399,690, which was filed Mar. 6, 2009 and has issued as U.S. Pat. No. 8,206,822, and which is hereby incorporated by reference in their entireties. U.S. application Ser. No. 12/399,690 is a continuation in part of U.S. application Ser. No. 12/439,647, which was filed Mar. 2, 2009 and has issued as U.S. Pat. No. 8,206,816, and which is hereby incorporated by reference in their entireties. U.S. application Ser. No. 12/439,647 is a U.S. national stage entry application based on PCT/US2007/077146, which was filed Aug. 29, 2007 and which claims priority from U.S. provisional application Ser. No. 60/823,842, which was filed Aug. 29, 2006, the entire contents of each of which is hereby incorporated by reference in their entireties.

STATEMENT REGARDING FEDERALLY SPONSORED RESEARCH OR DEVELOPMENT

This invention was made with Government support under Grant No. DMR 0309441 awarded by the National Science Foundation. The Government has certain rights in the invention.

FIELD OF THE INVENTION

The present invention relates to methods and materials to shape articles comprising a polyelectrolyte complex.

BACKGROUND OF THE INVENTION

All solid materials exhibit viscoelastic behavior. The Maxwell model, which comprises an elastic element (spring) and a viscous element (dashpot) in series, illustrates viscoelasticity: for high frequency vibrations the Maxwell model predicts almost perfect elastic behavior, i.e., minimal energy dissipation, as the motion of the dashpot becomes negligible. For low or moderate frequencies the time scales of the viscoelastic relaxation and vibration are comparable, and they interfere destructively with one another, allowing for more efficient energy dissipation and damping.

The Young's modulus, E, (also known as elastic modulus, modulus of elasticity, or tensile modulus) is a measure of the stiffness of a material. E is the ratio between the tensile stress, $\sigma$, divided by the tensile strain, e. E is typically measured on a tensile apparatus which elongates a material and reports the stress needed to produce a certain strain. Alternatively, a sample is compressed and the required stress for a needed deformation is measured. E may be measured under static, or quasi-static, conditions, where the stress does not vary with time. Alternatively, the modulus can be measured under dynamic or time-varying conditions where a material may exhibit properties of elasticity and viscous flow (viscoelasticity) in which case the modulus depends on frequency of deformation and a complex modulus, $E^*$, is defined, where $E^*=E_1+iE_2$, where $E_1$ is the storage modulus, which is a measure of energy stored on a deformation cycle, and $E_2$ is the loss modulus, which is a measure of the energy lost on a cycle.

The shear modulus, G, (also referred to as the modulus of rigidity) of a material, measured under dynamic or time-varying conditions, is the ratio of the shear stress to the shear strain. The shear modulus is typically measured with a parallel-plate rheometer. If the shear rate changes, G depends on the frequency at which the shear changes. Therefore, a complex shear modulus is defined as $G^*=G_1+iG_2$, where $G_1$ is the storage modulus, which is a measure of energy stored on a deformation cycle, and $G_2$ is the loss modulus, which is a measure of the energy lost on a cycle. For isotropic materials, $E=3G$ for small deformations.

The ratio $E_1/E_2$ or $G_1/G_2$ is equal to $\tan(\Delta)$, the ratio of energy lost to energy stored in one cycle. $\tan(\Delta)$ is called the loss factor and is a measure of damping efficiency, with greater damping indicated by higher $\tan(\Delta)$.

Damping or shock-absorbing properties are not determined from static measurements. Damping properties are ascertained by time varying or periodic deformation of the sample. Thus, a soft material (low E) is not necessarily a good candidate for damping. Furthermore, a material that is effective for damping over a certain frequency range may not be effective for damping over another frequency range. Therefore, in reporting a complex modulus ($E^*$ or $G^*$), a frequency or frequency range is preferably specified.

Hydrogels comprise water and polymers and are useful for medical and pharmaceutical applications (e.g. see Peppas, N. A.; Editor, *Hydrogels in Medicine and Pharmacy, Vol. 3: Properties and Applications.* 1987; p 195 pp.). Hydrogels are usually held together via physical or chemical crosslinks, otherwise the polymers of which they are comprised would dissolve in the solvent (water). Polyelectrolyte complexes are interpenetrating complexes of one or more predominantly positive polyelectrolytes and one or more predominantly negative polyelectrolytes. The opposite charges on the polymers form ion pairs between chains, holding the chains together. This ion pairing is a type of physical crosslinking. Polyelectrolyte complexes in contact with aqueous solutions can be considered hydrogels with high crosslinking density.

Recent studies have evaluated the static mechanical properties of polyelectrolyte multilayers, which are ultrathin films of complexed polyelectrolytes. See, for example, Jaber, J. A. and Schlenoff, J. B., J. Am. Chem. Soc. 128, 2940-2947 (2006). Polyelectrolyte multilayers are intermolecular blends of positively and negatively charged polyelectrolyte, wherein each layer of polyelectrolyte added to a growing film has an opportunity to complex efficiently and completely with the existing material, excluding the maximum amount of water. The elastic modulus of these films ranges from kPa to MPa. However, these films are far too thin (a few micrometers or less) to be used for mechanical components in most systems. Furthermore, little is know of the dynamic mechanical properties of molecularly blended complexes of positive and negative polyelectrolytes.

There is a need to prepare articles with dimensions in the millimeter to centimeter to meter scale to provide materials and shapes for biomedical and engineering applications. Polyelectrolyte complexes are prepared in a straightforward manner by mixing solutions of positive and negative polyelectrolytes. However, the resulting precipitate is gelatinous and difficult to process. The dried complexes, for example, are generally infusible and therefore cannot be injection molded or reformed into articles under elevated temperatures. Michaels (U.S. Pat. No. 3,324,068) has disclosed the used of non-volatile plasticizers such as nonvolatile acids, organic oxysulfur compounds and organic oxyphosphorous compounds to decrease the brittleness of polyelectrolyte complexes when they are dried. U.S. Pat. No. 3,546,142 describes a method for creating solutions of polyelectrolyte complexes using aggressive ternary solvents which are mixtures of salt, water and organic solvent. Said solutions of complexes may be reformed into solids by diluting the solution, or by evaporating the solvent (film casting). Mani et al. (U.S. Pat. No. 4,539,373) point out that the solid complexes "are not thermoplastic, i.e. they are not moldable or extrudable, so they must be handled as solutions." Mani et al. disclose a polyelectrolyte complex comprising thermoplastic repeat units which can be thermally molded.

Polyelectrolyte complexes have been proposed as tissue engineering scaffolding (e.g., see Lim and Sun, Science, 210: 908-910 (1980) and Yu et al., U.S. Pat. No. 6,905,875). The purpose of a tissue engineering scaffold is to support and maintain growing cells. Thus, these scaffolds are usually soft and porous and, therefore, not well suited for use as a compressive mechanical support.

SUMMARY OF THE INVENTION

Among the various aspects of the present invention may be noted method of forming an article comprising a polyelectrolyte complex, the polyelectrolyte complex comprising an interpenetrating blend of at least one predominantly positively charged polyelectrolyte and at least one predominantly negatively charged polyelectrolyte. The method comprises contacting the article with a first solution to change a salt doping level ratio within the polyelectrolyte complex from an initial salt doping level to a second salt doping level, wherein the salt doping level ratio is changed by varying one or more factor selected from the group consisting of salt type, salt concentration, temperature, and pH within the complex; and applying a mechanical force to the article at the second salt doping level in order to reform the complex into a persistent shape. The second salt doping level ratio is between about 0.50 and about 0.990 and the article is fully hydrated when the mechanical force is applied.

Another aspect of the present invention is a method for preparing an article comprising a polyelectrolyte complex. The method comprises combining the predominantly positively-charged polyelectrolyte and the predominantly negatively charged polyelectrolyte in a solution having a salt of concentration sufficient to form a polyelectrolyte complex having a doping level ratio between about 0.5 and about 0.990. In addition, a mechanical force is applied to reform the polyelectrolyte complex and thereby form an article comprising the compacted polyelectrolyte complex. Said article has uniform composition and is not weakened by grain boundaries between poorly-fused particles.

Another aspect of the invention is an article comprising a polyelectrolyte complex, the polyelectrolyte complex comprising an intermolecular blend of a predominantly positively-charged polyelectrolyte and a predominantly negatively charged polyelectrolyte and being free of salt crystals the article having no transverse dimension less than about 100 micrometers, the article further comprising one or more additives selected from the group consisting of metal oxide particles, silicon oxide, zirconium oxide, clay minerals, carbon power, graphite, carbon fibers, carbon nanotubes, polymer fibers, cellulose fibers, and combinations thereof.

Yet another aspect of the invention is an article comprising a polyelectrolyte complex, the polyelectrolyte complex comprising an intermolecular blend of a predominantly positively-charged polyelectrolyte and a predominantly negatively charged polyelectrolyte and being free of salt crystals, the article further comprising magnetic particles having at least one transverse dimension between about 1 nanometer about 100 micrometers.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE EMBODIMENTS OF THE INVENTION

Figure 1:
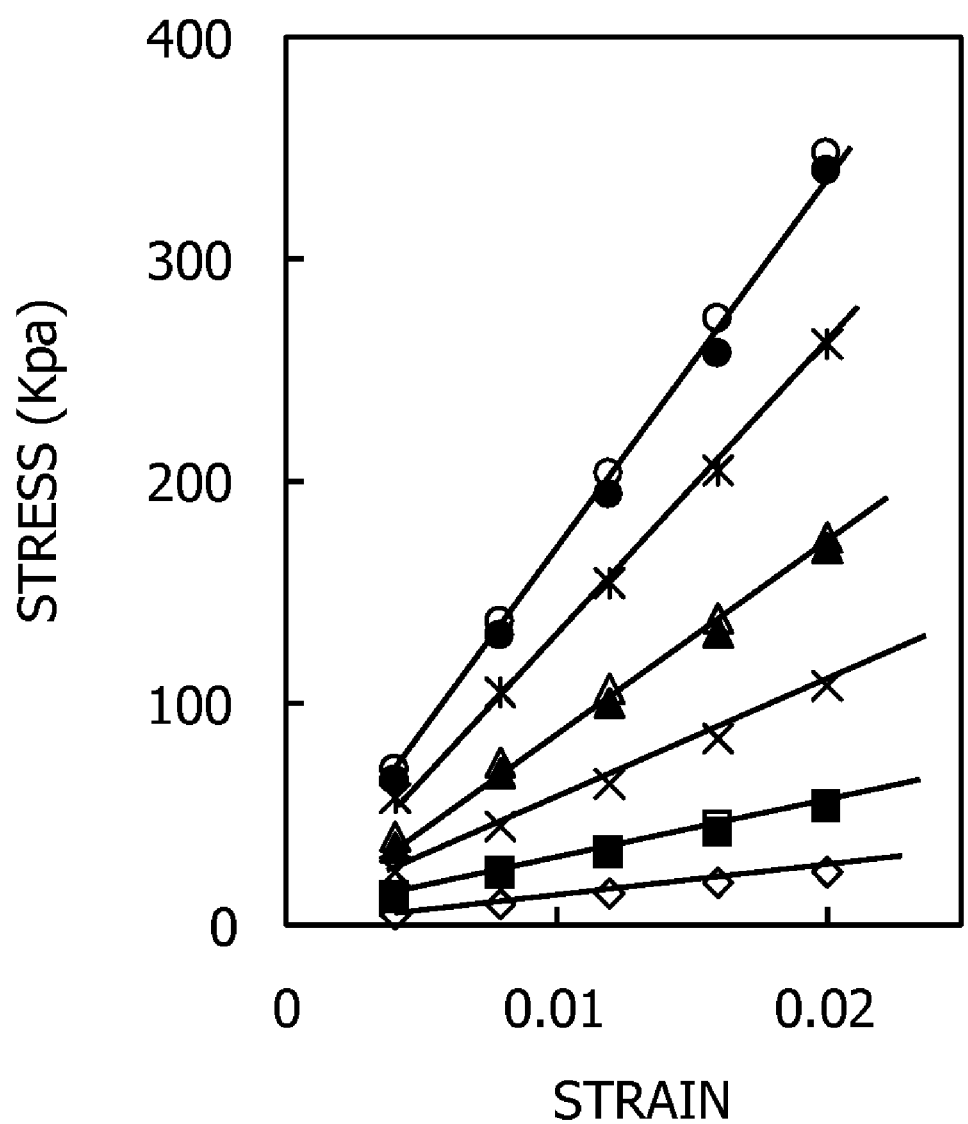
FIG. 1 is graph showing the stress-strain behavior of a polyelectrolyte complex after conditioning at several ionic strengths. The data in the graph were obtained according to the method of Example 1.

One aspect of the invention is an article comprising a polymer, in particular, a polymer known as a "polyelectrolyte" that comprises multiple electrolytic groups that dissociate in aqueous solutions, making the polymer charged. The article of the present invention comprises a polyelectrolyte complex, that is, an intermolecular blend of a predominantly positively-charged polyelectrolyte and a predominantly negatively-charged polyelectrolyte. The polyelectrolyte complex is preferably compacted, such as by centrifugation or pressure, in a manner that increases the density of the polyelectrolyte complex to a value substantially greater than that which may be obtained following precipitation. Moreover, the article may be reformed or reshaped to have dimensions typically on the order of millimeters to centimeters, which is also substantially greater than that achievable by conventional multilayering and intermixing methods. We have discovered that fully hydrated (i.e. complexes in contact with water) polyelectrolyte complexes may be reformed into shapes without raising the temperature, without the addition of organic solvent, and without the need for dissolution, if they are doped with salt ions to a sufficient extent. We have further discovered that the as-precipitated polyelectrolyte complex may be partially compacted or densified by mechanically working the complex. Accordingly, the complex may be mixed, agitated, folded, kneaded, or stirred at close to room temperature. Thus, the polyelectrolyte complex is preferably worked until its modulus is at least a factor of ten greater than in the freshly-precipitated state.

The method according to the present invention provides for producing articles comprising compact blends of positively-charged polyelectrolytes and negatively-charged polyelectrolytes in intricate or detailed or extended geometries at about room temperature using conditions that avoid the use of organic solvents.

In one embodiment, the force for compacting the blends of positively-charged polyelectrolytes and negatively-charged polyelectrolytes is provided by a centrifugal field and the article adopts the shape of the container in which it is centrifuged. In another embodiment, the force for compacting the blends of positively-charged polyelectrolytes and negatively-charged polyelectrolytes is provided by hydrostatic pressure by means of a piston, syringe, screw, or rollers. In yet another embodiment the polyelectrolyte complex article comprises magnetic particles and the force for compacting the blends of positively-charged polyelectrolytes and negatively-charged polyelectrolytes is created by a magnetic field. In still another embodiment, the article is formed by forcing a material comprising a salt-doped interpenetrating blend of positively-charged polyelectrolytes and negatively-charged polyelectrolytes into a mold under pressure and said article adopts and maintains the contours of the mold following release from the mold. In still another embodiment, the article is formed by forcing a material comprising a salt-doped interpenetrating blend of positively-charged polyelectrolytes and negatively-charged polyelectrolytes through an orifice, said orifice defining the cross section of the article as it passes through the orifice.

In accordance with one aspect of the present invention, it has been discovered that increasing the salt concentration within the bulk of the fully hydrated polyelectrolyte complex by contacting it with a sufficiently high concentration of salt, renders the complex flowable without resorting to a change in temperature or other conditions. Under such flowable conditions the complex may be reshaped into a second persistent shape. Conversely, decreasing the salt concentration with the bulk of the polyelectrolyte complex causes the complex to revert to a non-flowable state. Advantageously, the transformation of the complex into a flowable material takes place without recourse to elevated temperatures and without the requirement for organic solvents or acids or organic plasticizers. Conditions which avoid elevated temperatures and/or acids and/or organic plasticizers are preferred when reforming the polyelectrolyte article under physiological conditions. Additionally, conditions which avoid elevated temperatures and/or acids and/or organic plasticizers are preferred when the polyelectrolyte article comprises temperature-sensitive organic molecules, such as paclitaxel, or biomolecules, such as enzymes and growth factors. Accordingly, the dynamic mechanical properties of an article comprising the polyelectrolyte complex may be initially controlled by controlling the salt concentration during the preparation of the polyelectrolyte complex and then altered by increasing or decreasing the salt concentration of the solution contacting the article after preparation. Thus, for example, a flowable compacted article may be prepared in the presence of high salt concentration, and then injected into a mold. Once the flowable article is in the mold, or has been removed from the mold, a concentration gradient may be applied by contacting the reshaped article with a solution having a lower salt concentration, which thereby causes salt located in the bulk of the article to diffuse out into the solution, making the compacted article less flowable, thereby causing an increase in the modulus of the article, which is defined by the inner surfaces of the mold.

The method described herein of creating a moldable polyelectrolyte complex is "environmentally friendly." That is, all processing may be performed in aqueous solutions comprising no volatile organic compounds (VOCs). The salt used to dope the polyelectrolyte complex may be a common material of low toxicity, such as NaCl.

In one aspect of this invention, a polyelectrolyte complex is compacted and reshaped into a useful article using the method described herein. Then, instead of discarding the article after it has been used, the article is further reshaped into a second useful article using the method described herein. In this way, the polyelectrolyte material, a valuable polymer derived from petrochemicals or natural sources, may be recycled. Recycling is considered environmentally friendly or a "green" process.

In general, the polyelectrolyte complex is formed by combining a predominantly negatively-charged polyelectrolyte and a predominantly positively-charged polyelectrolyte. In a preferred embodiment, the formation of the article involves combining separate solutions, each containing at least one of the polyelectrolytes; in this embodiment, at least one solution comprises at least one predominantly positively-charged polyelectrolyte, and at least one solution comprises at least one predominantly negatively-charged polyelectrolyte. Either or both of these solutions may comprise salt ions or additives. The formation of a polyelectrolyte complex, $Pol^+Pol^-$, by mixing individual solutions of the polyelectrolytes in their respective salt forms, $Pol^+A^-$ and $Pol^-M^+$, may be represented by the following equation:

$$Pol^+A^- + Pol^-M^+ \rightarrow Pol^+Pol^- + MA$$

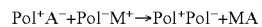

wherein $M^+$ is a salt cation, such as sodium, and $A^-$ is a salt anion such as chloride. $Pol^-$ and $Pol^+$ represent repeat units on predominantly negatively-charged polyelectrolytes and predominantly positively-charged polyelectrolytes, respectively. According to the equation, the process of complexation releases salt ions into external solution, which are then part of the salt solution concentration.

Separate solutions containing the polyelectrolytes are preferably combined in a manner that allows the positively charged polyelectrolyte(s) and the negatively charged polyelectrolyte(s) to intermix. Intermixing the respective polyelectrolytes causes the in situ formation of a polyelectrolyte complex comprising an intermolecular blend of the positively charged polyelectrolyte and the negatively charged polyelectrolyte. Preferably, at least one of the solutions comprises salt ions, such that salt ions also intermix with and become part of the polyelectrolyte complex. The resulting polyelectrolyte complex may simply be allowed to precipitate and settle to the bottom of the container. The supernatant is, in a preferred embodiment, separated to the extent possible from the polyelectrolyte complex. The precipitate formed after mixing said solutions is gelatinous and of poor structural integrity.

Individual polyelectrolyte solutions that are mixed may themselves comprise mixtures of polyelectrolytes. For example, a solution may comprise two positively-charged polyelectrolytes with two distinct chemical compositions. When the mixture of positively-charged polyelectrolytes is mixed with the negatively-charged polyelectrolyte solutions the resulting complex will incorporate a blend of the two positive polyelectrolytes. Such a strategy is described for example in Z. Sui, J. B. Schlenoff, Langmuir vol. 18, p 8263 (2003).

The precipitated polyelectrolyte complex is preferably compacted. In one embodiment, compacting may be accomplished by centrifugation, such that the polyelectrolyte complex is compacted into a plug of material inside the centrifuge vessel. In a preferred embodiment, salt is present during compaction. In another preferred embodiment, the polyelectrolyte complex is densified by allowing mechanical agitation or working of the complex. In yet another preferred embodiment, compaction of the complex is achieved by exposing the complex to a solution of high osmotic stress, as described in U.S. Provisional Application Ser. No. 61/089,286.

Polyelectrolytes for Complexes

The charged polymers (i.e., polyelectrolytes) used to form the complexes are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive repeat units and negative repeat units distributed throughout the polymer in a random, alternating, or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic. An example of a zwitterionic repeat unit is 3-[2-(acrylamido)-ethyldimethyl ammonio]propane sulfonate, AEDAPS. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units.

The charges on a polyelectrolyte may be derived directly from the monomer units, or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof; polycarboxylates such as poly(acrylic acid) (PAA) and poly(methacrylic acid), polyphosphates, and polyphosphonates.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH) and polyethyleneimine (PEI); polysulfoniums, and polyphosphoniums.

Exemplary polyelectrolyte repeat units, both positively charged and negatively charged, are shown in Table I.

TABLE I

Polyelectrolyte Repeat Units

| Name | Structure |
|---|---|
| diallyldimethylammonium (PDADMA) | 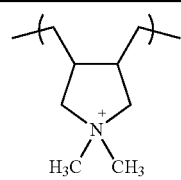 |

TABLE I-continued

Polyelectrolyte Repeat Units

| Name | Structure |
|---|---|
| styrenesulfonic acid (PSS) | 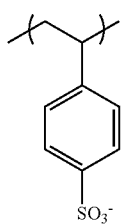 |
| N-methyl-2-vinyl pyridinium (PM2VP) | 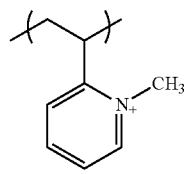 |
| N-methyl-4-vinylpyridinium (PM4VP) | 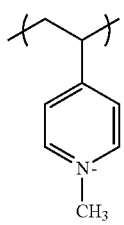 |
| N-octyl-4-vinylpyridinium (PNO4VP) | 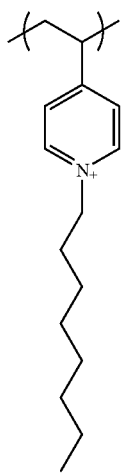 |
| N-methyl-2-vinyl pyridinium-co-ethyleneoxide (PM2VP-co-PEO) | 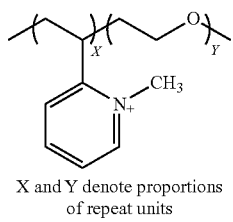<br>X and Y denote proportions of repeat units |
| acrylic acid (PAA) | 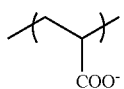 |

TABLE I-continued

Polyelectrolyte Repeat Units

| Name | Structure |
|---|---|
| allylamine (PAH) | 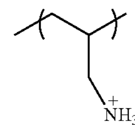 |
| ethyleneimine (PEI) | 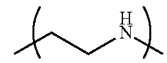 |

Further examples of oppositely-charged polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate, carrageenin, sulfonated lignin, and carboxymethylcellulose.

Natural, or biological, polyelectrolytes typically exhibit greater complexity in their structure than synthetic polyelectrolytes. For example, proteins may comprise any combination of about 2 dozen amino acid building blocks. Polymeric nucleic acids such as DNA and RNA may also comprise many different monomer repeat units. The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte solution typically comprises about 0.01% to about 50% by weight of a polyelectrolyte, and preferably about 1% to about 20% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention. Block polyelectrolytes, wherein a macromolecule comprises at least one block of charged repeat units, are also suitable. The number of blocks may be 2 to 5. Preferably, the number of blocks is 2 or 3. If the number of blocks is 3 the block arrangement is preferably ABA.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Even if polyelectrolyte complexes are prepared by mixing organic-soluble and water-soluble polymers, the complex is preferably rinsed to remove organic solvents before it is reshaped according to the method described herein. Some organic solvents are hard to remove even with extensive rinsing. Therefore, the preferred solvent for polyelectrolyte complexation is water.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride) and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallydim- ethylammonium chloride), poly(N-methylvinylpyridinium) and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

The charged polyelectrolyte may be a synthetic copolymer comprising pH sensitive repeat units, pH insensitive repeat units, or a combination of pH sensitive repeat units and pH insensitive repeat units. pH insensitive repeat units maintain the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte at the surface of, or within, a polyelectrolyte complex.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly (acrylic acids), poly(methacrylic acids), poly(carboxylic acids), and copolymers thereof. Additional preferred polyelectrolytes comprise protonatable nitrogens, such as poly (pyridines), poly(imidazoles), poly(piperidines), and poly (amines) bearing primary, secondary or tertiary amine groups, such as poly(allylamine).

To avoid disruption and possible decomposition of the polyelectrolyte complex, polyelectrolytes comprising pH sensitive repeat units additionally comprise pH insensitive charged functionality on the same molecule. In one embodiment, the pH insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety ($-N^+R_aR_bR_c$ wherein $R_a$, $R_b$, and $R_c$ are independently alkyl, aryl, or mixed alkyl and aryl), a pyridinium moiety, a bipyridinium moiety or an imidazolium moiety, the sulfonium atom may be part of a sulfonium moiety (—S$^+$R$_d$R$_e$ wherein R$_d$ and R$_e$ are independently alkyl, aryl, or mixed alkyl and aryl) and the phosphonium atom may be part of a phosphonium moiety (—P$^+$R$_f$R$_g$R$_h$ wherein R$_f$, R$_g$, and R$_h$ are independently alkyl, aryl, or mixed alkyl and aryl). In another embodiment, the pH insensitive repeat unit is a negatively charged repeat unit selected from the group consisting of repeat units containing a sulfonate (—SO$_3^-$), a phosphate (—OPO$_3^-$), or a sulfate (—SO$_4^-$).

Exemplary negatively charged pH insensitive charged repeat units include styrenesulfonic acid, 2-acrylamido-2-methyl-1-propane sulfonic acid, sulfonated lignin, ethylenesulfonic acid, methacryloxyethylsulfonic acid, sulfonated ether ether ketone, phosphate. Preferred pH insensitive negatively charged polyelectrolytes include polyelectrolytes comprising a sulfonate group (—SO$_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof.

Exemplary positively charged pH insensitive repeat units include diallyldimethylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, a N-aryl vinyl pyridinium, alkyl- or aryl imidazolium, sulfonium, or phosphonium. Preferred pH insensitive positively-charged polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof.

For illustrative purposes, certain of the pH insensitive positively-charged moieties are illustrated below:

Pyridinium having the structure:

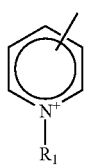

wherein R$_1$ is optionally substituted alkyl, aryl, alkaryl, alkoxy or heterocyclo. Preferably, R$_1$ is alkyl or aryl, and still more preferably R$_1$ is methyl;

Imidazolium having the structure:

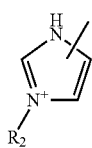

wherein R$_2$ is optionally substituted alkyl, aryl, alkaryl, alkoxy or heterocyclo. Preferably, R$_2$ is alkyl or aryl, and still more preferably R$_2$ is methyl;

Bipyridinium having the structure:

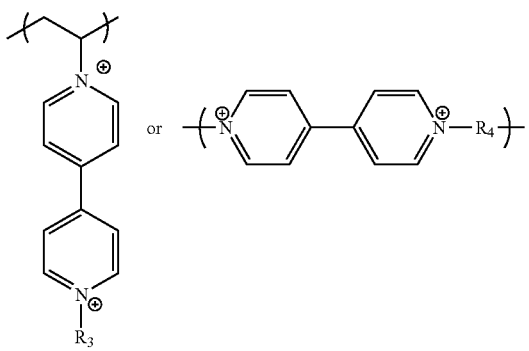

wherein R$_3$ and R$_4$ are optionally substituted alkyl, aryl, alkaryl, alkoxy or heterocyclo. Preferably, R$_3$ and R$_4$ are alkyl or aryl, and still more preferably R$_3$ is methyl.

The pH insensitive polyelectrolyte may comprise a repeat unit that contains protonatable functionality, wherein the functionality has a pKa outside the range of experimental use. For example, poly(ethyleneimine) has protonatable amine functionality with pKa in the range 8-10, and is thus fully charged (protonated) if the experimental conditions do not surpass a pH of about 7.

Preferably, the pH insensitive groups constitute about 10 mol % to about 100 mol % of the repeat units of the polyelectrolyte, more preferably from about 20 mol % to about 80 mol %. Preferably, the pH sensitive groups constitute about 30 mol % to about 70 mol % of the repeat units of the polyelectrolyte.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table II. Preferred uncharged repeat units also include N-isopropylacrylamide and propylene oxide.

TABLE II

| Neutral Repeat Units | |
|---|---|
| Name | Structure |
| Acrylamide | |
| Isopropylacrylamide | |
| Vinylpyrrolidone | |

TABLE II-continued

Neutral Repeat Units

| Name | Structure |
|---|---|
| Ethylene oxide | (structure) |
| Propylene oxide | (structure) |
| Vinylcaprolactam | (structure) |

Protein adsorption is driven by the net influence of various interdependent interactions between and within surfaces and biopolymer. Possible protein-polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, proteins are remarkably tenacious adsorbers, due to the other interaction mechanisms at their disposal. It is an object of this invention to show how surfaces may be selected to encourage or discourage the adsorption of proteins to centrifugally compacted polyelectrolyte complexes when they are used in vivo. Protein adsorption may be discouraged by copolymerizing with vinyl repeat units having hydrophilic groups, vinyl repeat units having zwitterionic groups, and hydrophilic repeat units.

It is also known by those skilled in the art that zwitterionic functional groups are also effective at resisting the adsorption of biomacromolecules, such as proteins (e.g. see Holmlin et al. *Langmuir*, 17, 2841 (2001)). In one embodiment of this invention, centrifugally compacted polyelectrolyte complex articles also comprise zwitterionic functional groups. It has been found that polymers comprising zwitterionic functional groups alone do not form polyelectrolyte complexes if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 100 and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio]propane sulfonate) (PAEDAPS) and poly(N-propane sulfonate-2-vinyl pyridine) (P2PSVP). The structures of these zwitterions are shown in Table III.

TABLE III

Zwitterionic Repeat Units

| Name | Structure |
|---|---|
| 3-[2-(acrylamido)-ethyldimethyl ammonio] propane sulfonate (AEDAPS) | (structure) |
| N-propane sulfonate-2-vinyl pyridine (2PSVP) | (structure) |

It has been disclosed by Graul and Schlenoff (*Anal. Chem.*, 71, 4007 (1999)) that polyelectrolyte films prepared by the multilayering method are able to control the adsorption of protein. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred ratio of charged to neutral blocks in a polyelectrolyte complex from 10:1 to 1:4, and a more preferred ratio is 5:1 to 1:2.

In some applications, the compacted article comprises polyelectrolyte that renders the article biocompatible. Preferred polyelectrolytes for biocompatibility comprise fluorinated polymers, preferably fluorinated polyelectrolytes. See, for example, U.S. Pub. No. 2005/0287111, the entire contents of which are hereby incorporated in their entirety. Fluorinated polyelectrolytes are preferably copolymers, or copolyelectrolytes, comprising fluorinated and non-fluorinated repeat units. Said repeat units may be disposed in a random or block fashion on the backbone of said copolyelectrolytes. Preferred fluorinated copolyelectrolytes comprise charged non-fluorinated with noncharged fluorinated repeat units, or charged fluorinated with noncharged nonfluorinated repeat units. Other preferred fluorinated polyelectrolytes comprise charged fluorinated repeat units with charged nonfluorinated repeat units. Fluorinated copolyelectrolytes are preferably made by post-polymerization reactions on polymers, such as alkylation, or by polymerization of fluorinated monomers or mixtures of fluorinated monomers. Mole percentages of fluorinated repeat units on fluorinated copolyelectrolytes are preferably from 10% to 95%, and more preferably from 20% to 95%.

For illustrative purposes, certain fluorinated moieties are shown as vinyl repeat units:

Vinyl Polymer Repeat Unit

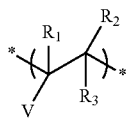

wherein $R_1$, $R_2$, and $R_3$ are each independently $-(CH_2)_mH$ or $-(CH_xF_{2-x})_nF$ and m and n are independently 0 to 12, x is 0, 1, or 2 and V is a group selected from among the following:

fluorinated hydrocarbons having the structure:
$-(CH_2)_p(CF_2)_qF$,
$-(CH_2)_p(CF_2)_qCOOH$,
$-(CH_2)_p(CF_2)_qOPO_3^-$,
$-(CH_2)_p(CF_2)_qSO_3^-$,
$-(CH_2)_p(CF_2)_qOSO_3^-$,
$-O(CH_2)_p(CF_2)_qF$,
$-O(CH_2)_p(CF_2)_qSO_3^-$,
and wherein p is 0 to 6 and q is 1 to 21;

fluorinated amides having the structure:

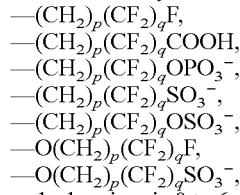

wherein $R_4$ is $-(CH_2)_p(CF_2)_qF$,
$-(CH_2)_p(CF_2)_qCOOH$,
$-(CH_2)_p(CF_2)_qOPO_3^-$,
$-(CH_2)_p(CF_2)_qSO_3^-$,
$-(CH_2)_p(CF_2)_qOSO_3^-$,
and wherein p is 0 to 6 and q is 1 to 21;

fluorinated esters having the structure:

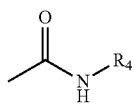

wherein $R_5$ is $-(CH_2)_p(CF_2)_qF$,
$-(CH_2)_p(CF_2)_qCOOH$,
$-(CH_2)_p(CF_2)_qOPO_3^-$,
$-(CH_2)_p(CF_2)_qSO_3^-$,
$-(CH_2)_p(CF_2)_qOSO_3^-$, and wherein p is 0 to 6 and q is 1 to 21;

fluorinated phenyl groups having the structure:

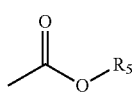

wherein n is 2 to 5; or

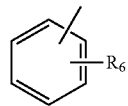

wherein $R_6$ is $-(CH_2)_p(CF_2)_qF$ or $-O(CH_2)_p(CF_2)_qF$ and wherein p is 0 to 6 and q is 1 to 21;

fluorinated pyridiniums having the structure:

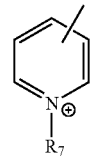

wherein $R_7$ is $-(CH_2)_p(CF_2)_qF$ and wherein p is 0 to 6 and q is 1 to 21;

fluorinated imidazoliums having the structure:

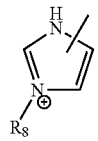

wherein $R_8$ is $-(CH_2)_p(CF_2)_qF$ and wherein p is 0 to 6 and q is 1 to 21;

fluorinated quaternary nitrogens having the structure:

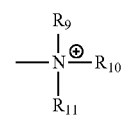

wherein $R_9$, $R_{10}$, and $R_{11}$ are each independently $-(CH_2)_p(CF_2)_qF$ and wherein p is 0 to 6 and q is 1 to 21 or -arylF$_z$ wherein z is 2 to 8;

fluorinated sulfoniums having the structure:

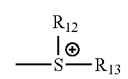

wherein $R_{12}$ and $R_{13}$ are each independently $-(CH_2)_p(CF_2)_qF$ wherein p is 0 to 6 and q is 1 to 21 or -arylF$_z$ wherein z is 2 to 8; and fluorinated phosphoniums having the structure:

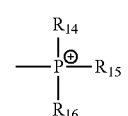

wherein $R_{14}$, $R_{15}$, and $R_{16}$ are each independently $-(CH_2)_p(CF_2)_qF$ wherein p is 0 to 6 and q is 1 to 21 or -arylF$_z$ where z=2 to 8.

For illustrative purposes, certain of these moieties are shown as allyl repeat units (e.g., PDADMA):

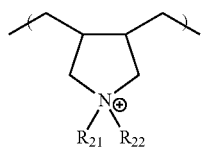

wherein $R_{21}$ and $R_{22}$ are $—(CH_2)_p(CF_2)_qF$, wherein p and q are independently selected for $R_{21}$ and $R_{22}$, and p is 0 to 6 and q is 1 to 21.

Table IV shows the structures of fluorinated polyelectrolytes that may be present in the polyelectrolyte complex articles of the present invention.

TABLE IV

Fluorinated Polyelectrolyte Repeat Units

| Name | Structure |
|---|---|
| 4-vinyl-trideca-fluoro-octyl pyridinium iodide-co-4-vinyl pyridine (PFPVP) | (structure shown) Where M is a mole fraction typically from about 0.1 to about 1.0, preferably from about 0.3 to about 0.8 |
| NAFION | (structure shown) Where X, Y, and X denote molar proportions; X may be from about 6 to about 10 parts, Y may be about 1 part and Z may be from about 1 to about 3 parts |

In one preferred embodiment, a small amount of chemical crosslinking is introduced into the reformed polyelectrolyte complex for stability. Chemical crosslinking is preferably accomplished by including difunctional monomers in the polyelectrolytes comprising the complex. For example, a divinyl repeat unit added to the polymerization reaction will be incorporated into two polyelectrolyte chains, giving a crosslink at the connection point. Alternatively, a reformed article may be treated with a difunctional crosslinking agent, such as $XCH_2-\phi-CH_2X$, where X is a halogen (Cl, Br, or I) and $\phi$ is a phenyl group. The phenyl group may be replaced by another aromatic or aliphatic moiety, and easily-diplaceable groups, such as toluene sulfonate, may replace the halogen. A preferred crosslinking agent is a dihalogenated compound, such as an aromatic or aliphatic dibromide, which is able to alkylate residual unalkylated units on two adjoining polyelectrolyte chains.

Another preferred method of chemical crosslinking a reformed polyelectrolyte complex is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of chemical crosslinking is preferably 0.01% to 50%, and more preferably 0.1% to 10%.

Another method of chemical crosslinking of a compacted polyelectrolyte complex is by photocrosslinking. Photocrosslinking may be achieved by the light-induced decomposition or transformation of functional groups that form part of the polymer molecules. See, for example, Strehmel, Veronika, "Epoxies: Structures, Photoinduced Cross-linking, Network Properties, and Applications"; Handbook of Photochemistry and Photobiology (2003), 2, 1-110. See also Allen, Norman S., "Polymer photochemistry", Photochemistry (2004), 35, 206-271; Timpe, Hans-Joachim "Polymer photochemistry and photocrosslinking" Desk Reference of Functional Polymers (1997), 273-291, and Smets, G., "Photocrosslinkable polymers", Journal of Macromolecular Science, Chemistry (1984), A21 (13-14), 1695-703. Alternatively, photocrosslinking of a polyelectrolyte complex may be accomplished by infusing the reformed polyelectrolyte complex with a small photoactive crosslinker molecule, then exposing the polyelectrolyte complex to light.

In some embodiments, the polyelectrolyte complex comprises further physical crosslinks created by hydrogen bonding. Hydrogen bonding is weaker than chemical bonding and occurs between a hydrogen bond donor and a hydrogen bond acceptor. Hydrogen bonds are minimally impacted by the presence of salt and thus the level of physical crosslinking due to hydrogen bonding remains substantially the same as the salt concentration is varied. Accordingly, the polyelectrolyte complex further comprises polymer repeat units capable of hydrogen bonding. Examples of hydrogen bond donor/acceptor pairs are presented in U.S. Pat. No. 6,740,409 and U.S. Pat. No. 7,470,449 as well as U.S. Pat. Pub. No. 20050163714.

Salt Content

In one embodiment, the compacted polyelectrolyte complex of the present invention may be reshaped in a manner that incorporates a significant salt ionic concentration within the bulk of the compacted article. The salt ionic concentration is preferably achieved by reshaping compacted articles in contact with solutions comprising salt ions. Stated differently, the polyelectrolyte complex is doped with salt ions to increase the ionic strength and decrease the extent of ionic crosslinking of the polyelectrolyte complex. The extent of doping and the identity of the salt ions may be varied precisely to advantageously control the reforming characteristics of the polyelectrolyte complex. Sources of salt ions for doping include the polyelectrolyte material, and from salt. Salts include soluble, ionic compounds that dissociate in solution to stable ions (e.g., sodium chloride). A salt may comprise organic ions, inorganic ions, or a combination of organic and inorganic ions. For physiological applications, ions selected to control mechanical properties are preferably of minimal toxicity. Anions and/or cations with charge greater than one are preferred for inducing greater doping at lower concentration.

A wide variety of salt ions may be added to the compacted polyelectrolyte complex to induce doped reshapable materials in the method of the present invention. In general, the salt may comprise any cation selected from among the alkali metal cations, alkaline earth metal cations, transition metal cations, semi-metallic cations, and organic cations such as amines. The salt(s) may comprise a mixture of two or more of any of these cations. Among the alkali metal cations, lithium, sodium, potassium, and rubidium may be incorporated into the compacted article, with sodium and potassium being particularly preferred. In certain physiological applications, the choice of alkali metal cations may be limited to sodium or potassium ions. Among the alkaline earth metal cations, magnesium, calcium, strontium, and barium may be incorporated into the compacted article. Calcium and magnesium cations are particularly preferred, and for physiological applications, the choice of alkaline earth metal cations may be limited to calcium and magnesium. A wide variety of transition metals may be incorporated into the compacted article including scandium, yttrium, titanium zirconium, vanadium, niobium, chromium, molybdenum, manganese, iron, ruthenium, cobalt, rhodium, nickel, palladium, platinum, copper, silver, gold, and zinc. In certain physiological applications, the choice of transition metal cations may be limited to zinc, silver, iron, and copper. Other metal cations that may be incorporated into the compacted articles include aluminum, indium, tin, lead, and bismuth. Organic cations that may be included include ammonium, primary, secondary, tertiary, and quaternary amines comprising alkyl groups having from one to four carbon atoms. Primary amines, secondary amines, and tertiary amines are protonated to achieve positive charge and are thus pH sensitive. Exemplary primary amines, secondary amines, and tertiary amines are protonated forms of methylamine, dimethylamine, trimethyl amine, ethylamine, diethylamine, and triethylamine among others. Quaternary amines are pH insensitive groups. Exemplary quaternary amines include tetramethylammonium, tetraethylammonium, tetrapropylammonium, among others. In one embodiment, the amine is a linear polyamine such as ethylene diamine, diethylene triamine, dipropylene triamine, triethylene tetraamine, tripropylene tetraamine, tetraethylene pentaamine, tetrapropylene pentaamine, spermine, or spermidine.

The anion may be selected from among halide anions, oxoanions, and organic anions. A combination of anions may be incorporated into the compacted article. Halide ions that may be incorporated into the compacted article include fluoride, chloride, bromide, and iodide. Advantageously, any of these halides may be incorporated into compacted articles for use in physiological applications. In one preferred embodiment, the halide anion is chloride ion. In another preferred embodiment, the halide anion is chloride ion with a relatively low concentration of fluoride ion. Incorporation of a low concentration of fluoride ion is advantageous when the reshaped article is used in or near bone, such as in dental implants or in the intervertebral space. Oxoanions that may be incorporated into the compacted article include sulfonate, sulfate, sulfite, phosphate, phosphite, phosphonate, pyrophosphate, hypochlorite, chlorite, chlorate, perchlorate, iodate, periodate, bromate, borate, carbonate, nitrate, nitrate, aluminate, and manganate, among others. Organic anions that may be incorporated into the compacted article include carboxylates, such as citrate, lactate, acetate, benzoate, formate, malate, malonate, fumarate, oxalate, propionate, butyrate, tartrate, and valerate, phthalate, among others. Hydrophobic anions, such as those with a high hydrocarbon to charge ratio, are preferred for enhancing doping. Preferred organic anions for physiological applications include citrate and lactate. Organic solvent is optionally added to the aqueous salt solution during doping and during reforming as long as the doping level remains within the preferred range during the reforming step when force is applied.

In view of the above cations and anions, a wide variety of salts may be incorporated into the compacted articles of the present invention. Preferably, the salts are soluble in aqueous solution at a concentration at least sufficient to incorporate ions into the compacted article to an extent sufficient to achieve the desired doping level. In some embodiments, however, a relatively insoluble salt may be incorporated to impart some other desired characteristic, for example, biocompatibility. In these embodiments, the insoluble salt may be present in the polyelectrolyte solutions in a relatively low concentration and may be combined with another salt having high solubility. For example, calcium citrate has relatively low solubility (about 0.01 M in 0.1 M HCl). In certain applications, it may be desirable to include calcium citrate, but its limited solubility hinders its ability to substantially affect the article's elastic doping level. Therefore, the polyelectrolyte solution may further comprise a highly soluble salt, such as sodium chloride, for example, that will become incorporated in a high enough concentration to achieve the desired doping level.

Particularly preferred salts include chloride salts, citrate salts, and phosphate salts. Preferred chloride salts include sodium chloride, potassium chloride, magnesium chloride, calcium chloride, and aluminum chloride. Preferred citrate salts include trisodium citrate, disodium hydrogencitrate, sodium dihydrogencitrate, tripotassium citrate, dipotassium hydrogencitrate, potassium dihydrogencitrate, magnesium citrate, and calcium citrate. Preferred phosphate salts include trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, and magnesium phosphate.

As stated above, doping of the compacted polyelectrolyte complex affects the elastic and dynamic mechanical properties of the article comprising the complex, such as, for example, the elastic and complex shear modulus. It has been observed that increasing the salt concentration decreases the article's G*. Conversely, decreasing the salt concentration increases G*, making the article harder and tougher. It has also been observed that incorporation of cations and anions having multiple valences (i.e., an absolute charge of two or greater) for a given concentration decreases elastic modulus and G* to a greater extent than does incorporation of singly charged cations and anions. For example, incorporating calcium chloride into the compacted polyelectrolyte complex by maintaining it in a solution having a calcium chloride concentration of 0.2 M decreases the article's elastic and shear moduli to a greater extent than does maintaining the article in the presence of solution comprising sodium chloride at a concentration of 0.2 M. The difference between contacting the polyelectrolyte complex with calcium chloride and sodium chloride is due to the greater doping level afforded by the same concentration of calcium chloride.

The process of doping is defined as the breaking of ion pair crosslinks by salt ions entering the polyelectrolyte complex. Salt ions electrically compensate the charges on the polyelectrolytes. In such a compensation, the salt ions are termed counterions. Salt ions residing in pores or paired with other salt ions or present as crystals are not considered to be doping the polyelectrolyte complex and do not contribute to the doping level. The level or density of doping is therefore inversely related to the crosslink density. Advantageously, the breaking of ion pair crosslinks by doping is reversible and under thermodynamic control. In contrast, chemical crosslinks are often irreversible.

Preferably, the doping level of polyelectrolyte complexes is created and maintained by contacting the complex with a solution comprising salt ions of a specific concentration. Equilibration of the polyelectrolyte complex in the salt solution in which the complex is immersed may be fairly rapid, with durations typically on the order of between about 1 minute and about 30 minutes per millimeter thickness of the compacted polyelectrolyte complex article.

The extent to which ion pair crosslinks have been replaced by salt counterions within the bulk of the compacted article comprising polyelectrolyte complex may be quantified in terms of a doping level or doping level ratio, determined by dividing the sum of the ionic charge provided by salt ions acting as counterions by the sum of charge provided by the polymer repeat units. This ratio may be expressed in terms of a doping level percentage by multiplying the doping level ratio by 100. The lowest doping level is 0.0 (0%) wherein all the positively charged polyelectrolyte repeat units are paired with all the negatively charged polyelectrolyte repeat units, which corresponds to the maximum level (100%) of ionic crosslinking. The highest doping level is 1.0 (100%), where all charged polyelectrolyte repeat units are paired with a salt ion. When the doping level is 1.0 the polyelectrolytes are dissociated: phase separation can occur between components; additives can phase separate, and solutions do not maintain their shape when reformed. Therefore, a doping level of 1.0, wherein the polyelectrolyte complex is dissolved, or maintained in solution, as described in U.S. Pat. No. 3,546, 142, is not preferred.

The doping level can be measured, for example by infrared absorption spectroscopy (see. Farhat and Schlenoff, *Langmuir* 2001, 17, 1184; and Farhat and Schlenoff, *Journal of the American Chemical Society*, 2003, vol. 125, p. 4627.)

It has been shown quantitatively that the mechanical properties of articles comprising polyelectrolyte complex are influenced by the doping level. For example, Jaber and Schlenoff (e.g. see Journal of the American Chemical Society, 2006, vol. 128, p. 2940) analyzed the mechanical properties of articles comprising polyelectrolyte complexes using classical theories of rubber elasticity. The elastic modulus of articles comprising polyelectrolyte complexes decreased as they were doped with salt ions. In the doping level range studied, which was about 0 to about 0.4, the articles were elastically deformed, meaning that they regained their original shape when the deforming force was removed. The preferred doping level for reshaping a polyelectrolyte complex article in the method of the present invention is critically important. In order to reshape a polyelectrolyte complex article into a persistent shape the doping level must be sufficiently high. In the method of the present invention it has been discovered that a doping level of at least 0.5 is required for reforming a polyelectrolyte complex article into a persistent shape. Preferably, the doping level is between 0.6 and 0.990 and more preferably it is between 0.7 and 0.990. Stated in terms of a percentage, the doping level is preferably between about 60% and about 99.00, more preferably between about 70% and about 99.00. A doping level greater than 0.990 is to be avoided. To illustrate a doping level ratio calculation, suppose that a simple polyelectrolyte complex comprises a blend of one positively charged polyelectrolyte having 100 positively charged repeat units paired with one negatively charged polyelectrolyte having 100 negatively charged repeat units. Such a polyelectrolyte complex therefore has a total charge provided by the charged repeat units of 200. The number of ionic crosslinks is 100. This polyelectrolyte complex may be doped with salt ions which become associated with the charged repeat units. For example, if 10 sodium ions are associated with 10 negatively charged repeat units and 10 chloride ions are associated with 10 positively charged repeat units, the sum of charges provided by the salt ions is 20, and 10 ionic crosslinks have been broken. The doping level ratio is calculated by dividing the sum of charges of the salt ions by the sum of charges from the repeat units, i.e., 20/200=0.1, or 10%, stated as a doping level percentage. By way of further example, if 5 calcium ions (2+) are associated with 10 negatively charged repeat units and 10 chloride ions are associated with 10 positively charged repeat units, the sum of charges provided by the salt ions is 20 (=5×2 for the calcium+10 for the chloride) and the doping level ratio is 20/200=0.1, or 10%, stated as a doping level percentage. To achieve these doping levels, the article comprising the polyelectrolyte is preferably maintained in contact with a solution of the doping salt in water. The salt concentration employed during preparation and compaction includes those ions liberated from the polyelectrolytes by complexation.

In some embodiments, the doping level ratio in polyelectrolyte complex articles comprising pH dependent polyelectrolyte repeat units may be controlled by changing the state of protonation of said pH dependent polyelectrolyte repeat units. The state of protonation of the pH sensitive repeat units within the complex may be accomplished changing the pH of a solution in contact with the polyelectrolyte complex. A polyelectrolyte complex comprising pH sensitive repeat units is formed with a fixed number of repeat units. The number and number density of charged repeat units may vary, however, depending upon the solution pH in contact with the polyelectrolyte complex. At high pH, pH sensitive repeat units, such as those containing carboxylic acid groups are deprotonated and may be coupled with a cationic salt ion or with a positively charged repeat unit on a positively charged polyelectrolyte. If the complex is contacted with a solution having a low pH, the carboxylate group becomes protonated, thereby increasing the positive charges within the polyelectrolyte, or, stated another way, decreasing the negative charge. The change in pH may cause the doping level to change. For example, a negative polyelectrolyte comprising 80 sulfonate repeat units (not pH dependent) and 20 acrylic acid repeat units (pH dependent) may be complexed with a positive polyelectrolyte comprising 100 DADMA repeat units (not pH dependent) at pH 10, where the acrylic acid repeat units are charged (ionized). This example complex comprises 200 charges or 100 ion pair crosslinks. If the pH of a solution is now lowered to below the pKa of the acrylic acid (about 5) the acrylic acid units become protonated (uncharged). For example, the pH could be lowered to a value of 3. Because the negative charge in the complex has decreased due to the neutralization of the acrylic acid repeat units, chloride ions must enter the complex to balance the positive charges on the remaining DADMA units. These DADMA units are now doped (by chloride ions).

Twenty ion pair crosslinks have been lost. The charges provided by the salt ions (chloride) are 20, the total charges provided by the repeat units are 180, and the doping level is thus 20/180 or 0.11. The effect is the same for pH sensitive positively charged repeat units, such as primary amines. In this case, deprotonation by increasing pH will cause a decrease in positive charge, or, stated another way, an increase in negative charge, that will be offset by an increase in cationic salt ions, such as sodium ions or calcium ions, thus changing the doping level.

Crosslinked rubbery materials are normally not suitable for reshaping. Without being held to a particular theory, it is believed that, at the preferred doping levels, the timescale for breaking and reforming ion pair crosslinks is faster than the timescale for reorganizing the polymer molecules during the reshaping step. Thus, the crosslinking is dynamic enough to allow the material to adopt a new, persistent shape at the end of the preferred method.

Methods of Forming

The method of the present invention preferably starts with polyelectrolyte complex in a compact state. The compaction may be achieved by any combination of methods including those described in PCT/US2007/077146 published as WO 2008/027989 and U.S. Provisional Application Ser. No. 61/089,286, and/or by mechanically working a less dense morphology of the polyelectrolyte complex.

The polyelectrolyte is preferably maintained in a fully hydrated state during the method of the present invention preferably by contact with water. In the fully hydrated state chunks, pellets, pieces or other shapes or articles of compacted complex are fully swollen with water, that is their water content approaches the maximum it would achieve when immersed in water under the conditions of reforming. Pieces of complex that are wetted by a film of water and doped to the preferred level are considered fully hydrated, and are suitable for the present invention. Because dried pieces of polyelectrolyte complex are difficult to rehydrate, it is preferred that the compact polyelectrolyte complex materials be prepared by coprecipitation of individual polyelectrolytes and maintained in a hydrated state, preferably in contact with water.

Fully hydrated complexes have a water content that is at the maximum thermodynamically prescribed value for the complex in contact with an aqueous solution under given conditions of salt concentration, doping, and temperature. For example, a fully hydrated complex article of PSS/PDADMA with no voids contains about 7 water molecules for each PSS repeat unit when it is immersed in water at room temperature. In contrast, the same polyelectrolyte complex article when immersed in 1.0 M NaCl contains about 11 water molecules per PSS repeat unit at room temperature. When such a complex is removed from solution it remains fully hydrated if it remains wetted by a film of water or by a film of salt solution.

In the preferred method, the polyelectrolyte complex article or articles start with one doping level, preferably below 0.5, more preferably below 0.2. The doping level is then raised to a second doping level, preferably above 0.5, more preferably above 0.7, and below about 0.990. The doping level should not be so high, e.g., about 1.0, that the polyelectrolyte complex dissociates. A force is then applied to the article or articles in order to form them into a new shape.

In one preferred embodiment, the shape of the article at the end of the reforming step is defined by the contours of a mold, in the case where the doped polyelectrolyte complex is forced into a mold. If the process starts with a plurality of articles, these articles are fused into a single shape at the end of the process.

In another preferred embodiment, the doped polyelectrolyte is extruded through an orifice, which defines the shape of the cross section of the reshaped article. If the process starts with a plurality of articles, these articles are fused into a single shape at the end of the process, although it is understood that the shape can be cut off with a blade at any point during this preferred embodiment. Methods known to the art for extruding materials, such as forcing materials through a die or orifice via a piston or a screw, are suitable. The orifice may be of any geometry known to the art, including those geometries that enhance the alignment of high-aspect-ratio fillers during the extrusion step. The orifice and other components are preferably made from corrosion-resistant materials, such as stainless steel, plastic or ceramic. For a screw extruder, a continuous form may be produced as long as pieces of polyelectrolyte complex are fed into the extruder continuously. If the starting polyelectrolyte complex article is not doped to the preferred level the pieces of polyelectrolyte complex that are fed into the extruder will not fuse together efficiently.

In another preferred method the doped polyelectrolyte complex article comprises magnetic nanoparticles and a force is applied by a magnetic field, preferably of field strength in the range 0.1 to 60 Tesla, more preferably 1 to 10 Tesla, to draw the complex into a mold or through an orifice. During this preferred method, the magnetic domains are advantageously aligned. Preferred methods for applying a force may be combined. For example, a magnetic field may be applied in a direction perpendicular to, or parallel to, the direction of the force applied by hydrostatic pressure, and simultaneously with the hydrostatic pressure.

In yet another preferred embodiment, a pattern is embossed into an article of polyelectrolyte complex doped to the preferred level. Enbossing is performed with a metallic, polymeric or ceramic material with features from the nanometer to the millimeter size range. Such a pattern may be quite intricate, the reformed polyelectrolyte complex article faithfully reproducing the features of the embossing pattern. For example, a microchannel or a series of microchannels may be embossed into the polyelectrolyte complex. In another example, a series of features representing bits of data for storage may be embossed into the polyelectrolyte complex. For embossing purposes, the doped polyelectrolyte complex is preferably planar.

The temperature during the reforming step preferably does not differ widely from room temperature. Preferably, the temperature is between 0° C. and 100° C. More preferably, the temperature is between 20° C. and 80° C. and yet more preferably the temperature is between 20° C. and 60° C. For polyelectrolyte complexes comprising biological molecules which must be maintained close to physiological conditions the temperature during the reforming step is preferably maintained at 37° C.±10° C.

The preferred conditions lead to the preferred doping level within the polyelectrolyte complex article that is to be reshaped. The temperature may be increased to above room temperature to control the doping level for a polyelectrolyte complex article in contact with a solution with a fixed salt concentration. It has been shown (Bucur et al. Journal of the American Chemical Society 2006, vol 128, p. 13690) that the doping effectiveness for a particular salt increases as temperature increases. The doping effectiveness is quantified by an equilibrium doping constant, $K_d$. For example, $K_d$ increases from about 0.7 to about 2 on going from 4° C. to 60° C. for sodium nitrate doping of a PDADMA/PSS complex article. Thus, it is not "melting" but an increase in doping effectiveness that is responsible for an increased ability to reform a polyelectrolyte complex article when it is fully hydrated with water. The preferred doping levels are specified without reference to temperature.

Additives

Solid additives that may be incorporated into the polyelectrolyte complex are typically known to the art to modify the physical properties of materials. Additives include fillers and/or reinforcing agents and/or toughening agents, such as inorganic materials such as metal or semimetal oxide particles (e.g., silicon dioxide aluminum oxide, titanium dioxide, iron oxide, zirconium oxide, and vanadium oxide), clay minerals (e.g., hectorite, kaolin, laponite, montmorillonite), hydroxyapatite or calcium carbonate. For example, nanoparticles of zirconium oxide added to a polyelectrolyte solution or complex solution tend to improve the abrasion resistance of the article. See Rosidian et al., *Ionic Self-assembly of Ultra Hard $ZrO_2$/polymernanocomposite Films*, Adv. Mater. 10, 1087-1091. When a magnetic force is to be applied to reshape the polyelectrolyte complex article preferably comprises magnetic particles having at least one dimension in the size range between 2 nanometers and 100 micrometers. High aspect ratio fillers are preferred for stiffening a compacted article at a relatively low fill loading. Preferred high aspect ratio additives include, metal fibers, needle-like clay minerals, such as attapulgite, and carbon-based fibers such as carbon fibers or single or multiwalled carbon nanotubes. Other high aspect ratio materials having at least one dimension in the nanometer or micrometer range are suitable additives. Such high aspect ratio materials include polymer fibers, such as nylon, aramid, polyolefin, polyester, cotton, and cellulose fibers, as well as cellulose nanofibers. Biodegradable fibers are preferred when the reformed polyelectrolyte complex article comprises biodegradable polyelectrolytes. The weight % of additives in the polyelectrolyte complex article depends on many factors, such as the aspect ratio and the degree of modification of physical properties required. Accordingly, the solid additives may comprise between about 1 wt % and 90 wt % of the polyelectrolyte complex article.

Preferably additives are added prior to the preparation of the starting polyelectrolyte complex article. Negatively charge additives are preferably combined with solutions comprising negative charged polyelectrolytes prior to mixing with solutions comprising positively charged polyelectroltytes so that the additives and polyelectroltytes do not associate prematurely. Additives and individual polyelectrolytes are preferably thoroughly mixed in solution first under shear flow (as created by stirring or a homogenizer) with the proviso that the shear rate should not be sufficient to break up the polymer chains. If however, the polyelectrolyte stabilizes and assists in the dispersion of the additive it may be preferable to first mix additive and polyelectrolytes of opposite charge. For example, nanotubes can sometimes be dispersed better in solution if they are "wrapped" with polymers.

For physiological applications of the reshaped polyelectrolyte complex article other additives may be added during the method of the present invention. For example, articles that are to be implanted in vivo may optionally further comprise antibacterial and/or anti-inflammation and/or antirejection agents and/or growth factors. These additives respectively aid in reducing infection, inflammation or rejection of the implanted article. Examples of antibiotics are well known to the art and are to be found in E. M. Scholar, The antimicrobial drugs, New York, Oxford University Press, 2000 or the Gilbert et al., The Stanford Guide to Antimicrobial Therapy, Hyde Park, Vt., 2000, or the R. Reese, Handbook of Antibiotics, Philadelphia, Lippincot, 2000. Antibacterial agents include silver. Other additives are known to the art for promoting various biomedical properties. These include paclitaxel, seratonin, heparin, and anticlotting factors. Unlike additives used to modify the physical properties of the polyelectrolyte complex article, additives with biological or biomedical activity are typically added in lower concentration. Accordingly, such additives preferably comprise between 0.001% and 5% by weight of the polyelectrolyte complex article.

These additives are preferably mixed with one of the constituent polyelectrolytes solutions that are used to prepare the polyelectrolyte complex. The advantage of introducing additives prior to precipitation is that the additives are incorporated more uniformly throughout the polyelectrolyte complex.

Biocompatibility

It has been shown that certain polyelectrolytes or polymers are biocompatible. For example, a biocompatible polyelectrolyte multilayer, on which smooth muscle cells were grown, has been described by Schlenoff et al. (U.S. Pub. No. 2005/0287111), which is herein incorporated by reference. This multilayer comprised fluorinated polyelectrolyte complex, on which cells grow. However, the cells do not consume the fluorinated material. In one aspect of the present invention, therefore, the reformed polyelectrolyte complex article further comprises a surface stratum of fluorinated polyelectrolyte. The surface stratum is preferably obtained by immersing the reformed polyelectrolyte complex article in a solution of fluorinated polyelectrolyte. The process may be repeated with alternating positive and negative fluorinated polyelectrolytes to obtain a thicker surface stratum. In one embodiment, the alternating layering to build up the surface stratum comprising fluorinated polyelectrolyte may be repeated to deposit between about one and about 1000 positively and negatively charged fluorinated polyelectrolyte pairs, preferably between about one and about 250 positively and negatively charged fluorinated polyelectrolyte pairs.

Bioinertness

It has been shown that a polyelectrolyte complex film comprising a zwitterion repeat unit has bioinert properties, i.e., the adsorption of proteins, cells and other biological materials is minimized on the film. Examples are provided in U.S. Pub. No. 2005/0287111). Therefore, in one aspect of the present invention, the reformed polyelectrolyte complex article further comprises a surface stratum comprising polyelectrolytes comprising zwitterionic repeat units. Other bioinert materials are known to the art, such as poly(ethylene glycols), PEG. Therefore, in one aspect of this invention, the compacted polyelectrolyte complex article further comprises a surface stratum of PEG.

Other biological materials are known to be biocompatible, such as serum albumin. In one embodiment, the reformed polyelectrolyte complex article may be coated with serum albumin on exposure to in vivo conditions (i.e. following implant).

Having described the invention in detail, it will be apparent that modifications and variations are possible without departing from the scope of the invention defined in the appended claims.

EXAMPLES

The following non-limiting examples are provided to further illustrate the present invention.

In the examples, the following shorthand for polyelectrolyte complexes built on substrates is employed: $(A/B)_x$ where A is the starting polyelectrolyte contacting the substrate, B is the terminating polyelectrolyte in contact with subsequent protein solutions and x is the number of layer pairs. In $(A/B)_x$ A, A would be the terminating polymer. Salt, MY (cation M and anion Y), has an important role in the buildup process and is represented by $(A/B)_x$ @c MY, where c is the molarity of the salt (MY) in the polymer solution. The pH can be included in the nomenclature esp. when using pH dependent polyelectrolytes. For example, $(PAH/PAA)_2PAH$ @ 0.25 M NaCl @ pH 7.4, represent two layers pairs of PAH/PAA built at 0.25 M NaCl and a pH of 7.4.

Example 1

Static Stress-Strain Behavior of Polyelectrolyte Complex

Several compacted polyelectrolyte complexes were prepared by the multilayer method on a Teflon™ (perfluoropolymer) substrate. Free polyelectrolyte complexes were exposed to salt solutions of various concentrations for durations sufficient to equilibrate the bulk salt concentration of the polyelectrolyte complex with the salt solution. After equilibration, the elastic moduli of the polyelectrolyte complexes were measured.

Poly(styrene sulfonic acid) (PSS, molecular weight $6.8 \times 10^4$, $M_w/M_n = 1.06$) and poly(diallyldimethylammonium chloride) (PDADMA, molecular weight $3.7 \times 10^5$, $M_w/M_n = 2.09$) were obtained from Aldrich. Sodium chloride (NaCl) was obtained from Fisher. Deionized water (Barnstead, E-pure, Milli-Q) was used to prepare all aqueous solutions.

Two polyelectrolyte solutions were prepared, one comprising PSS and one comprising PDADMA. The polyelectrolyte concentration was 0.01 M (with respect to the monomer repeat unit) and the sodium chloride concentration was 1.0 M.

The poly(tetrafluoroethylene) (Teflon™) substrate (50 mm length×24 mm width×1.6 mm thickness) was cleaned in ethanol. The PDADMA/PSS polyelectrolyte complex was built upon the substrate according to the multilayer method by alternately exposing the substrate to the two polymer solutions for 5 minutes using a robotic platform (StratoSequence, nanoStrata Inc.) with three rinses of deionized water for 1 minute each. Rinse and polymer solution volumes were 50 mL. The polyelectrolyte complex was annealed at room temperature in a sodium chloride solution (1.0 M) for one week.

The "dry" thickness of the multilayer was determined using Fourier Transform Infrared Spectroscopy (FTIR) comparison (using the strong sulfonate stretch at 1100 cm$^{-1}$) of a PDADMA/PSS polyelectrolyte complex of known thickness (measured with a Gaertner Scientific L116S ellipsometer).

The PDADMA/PSS polyelectrolyte complex was peeled off the Teflon™ substrate using flat-ended tweezers and cut into microcoupons (2.0 mm length×150 μm width×9.0 μm dry thickness) with a razor blade. Both ends of a microcoupon were wrapped around aluminum foil clips and secured thereto by applying a drop of silicone rubber before closing the clips.

The aluminum clips were connected to minuten pin hooks on a capacitance-type force transducer (3.3 kHz resonant frequency; Aurora Scientific, Ontario, Canada, calibrated with small weights), and a moving iron galvanometer motor (step time ≦300 μs; Aurora Scientific, Ontario, Canada), designed for monitoring contractile behavior of single muscle fibers, mounted on the base of a Leitz Diavert (Wetzlar, Germany) inverted microscope. Silicone sealant was used to stabilize the clips on the minuten pins. Position was monitored by a capacitance-type transducer in the motor. Calibration was done by applying a control voltage input (square wave) to the motor, and measuring (using a microscope) the linear distance traveled in the horizontal plane by a clip attached to the motor hook. This allowed for rapid determination of the delta-position for a given input wave amplitude.

A temperature controlled stage containing six salt solutions of variable ionic strength (0.0 M, 0.2 M, 0.4 M, 0.6 M, 0.8 M. and 1.0 M sodium chloride) was used to soak the polyelectrolyte complex microcoupons for in situ measurements. Using these solutions at room temperature provides respective doping levels in the complex of about 0.0, 0.15, 0.25, 0.3, 0.35 and 0.45. Under these conditions the polyelectrolyte complex article was elastically deformed. The salt solutions were held in 200-μL anodized aluminum wells. The temperature was maintained at 28±1° C. with an ATR-4 regulator (Quest Scientific, North Vancouver, BC, Canada). Before every measurement, the polyelectrolyte complex microcoupon was conditioned in the salt solution for 10 minutes. Experimental control, data collection, and analysis of raw data were carried out using a PC-based system with a DT2831-G board (Data Translation, Marlboro, Mass.) and custom software. The software performs a fast Fourier transform method, converts to polar notation, finds the maximum amplitude index, calculates stiffness values and phase shift values, writes them to a file, converts to complex notation, and performs an inverse fast Fourier transform. Force was normalized to the polyelectrolyte complex microcoupon cross-sectional area, which was calculated from the wet thickness at different salt concentrations.

FIG. 1 shows the stress-strain behavior of the $(PDADMA/PSS)_{250}$@1.0M NaCl polyelectrolyte complex at different salt concentrations. The curves correspond to salt concentrations as follows: (open circle) 0.0 M NaCl solution; (asterisk) 0.2 M NaCl solution; (triangles) 0.4 M NaCl solution; (crosses) 0.6 M NaCl solution; (squares) 0.8 M NaCl solution; (diamonds) 1.0 M NaCl solution correspond to the stretching cycle (in increasing order of elongation) while (solid circles) 0.0 M NaCl solution; (solid triangles) 0.4 M NaCl solution; and (solid squares) 0.8 M NaCl solution indicate a decreasing elongation cycle.

Figure 2:
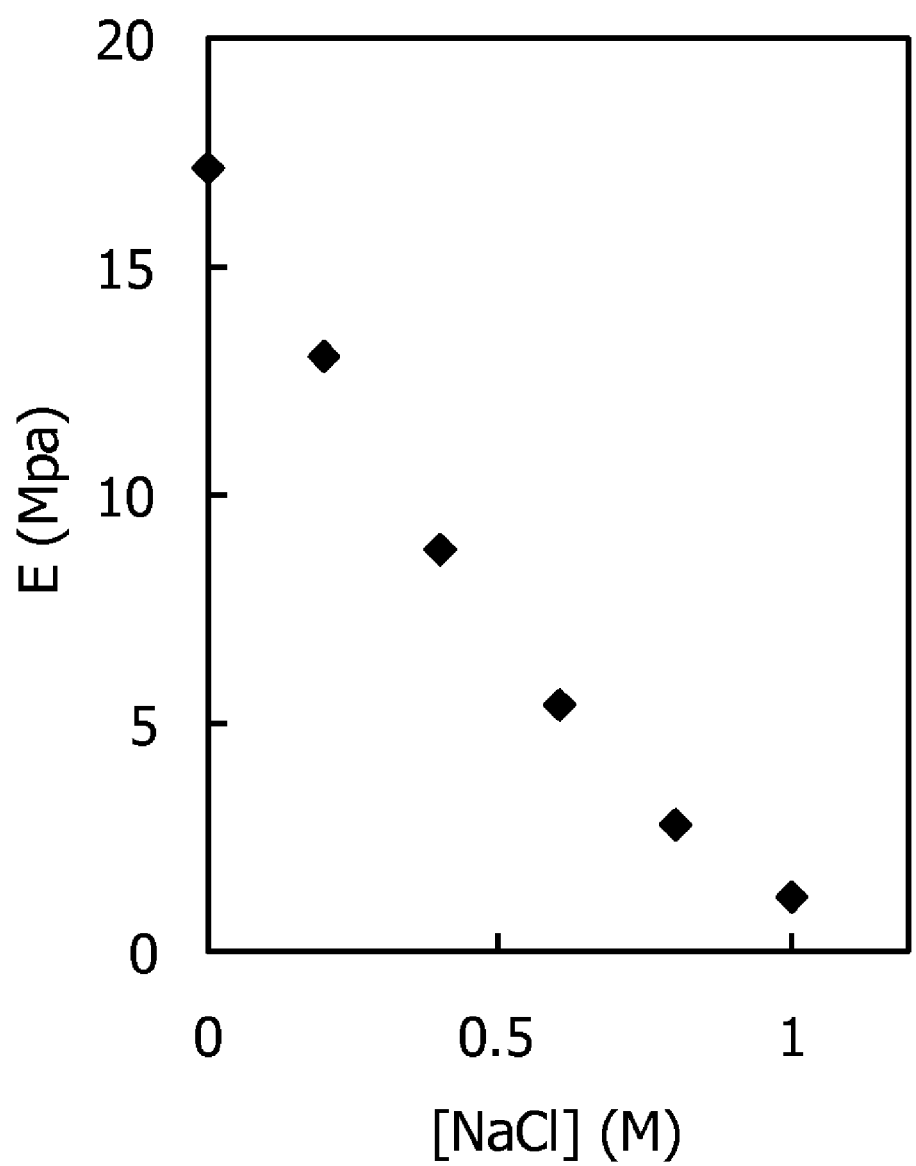
FIG. 2 is a graph showing the Elastic Modulus of a polyelectrolyte complex after conditioning at several ionic strengths. The data in the graph were obtained according to the method of Example 1.

FIG. 2 shows the elastic modulus, E, of the $(PDADMA/PSS)_{250}$@1.0M NaCl polyelectrolyte complex at different salt concentrations. The elastic modulus is obtained from the slope of the curves in FIG. 1. At 0.0 M NaCl, E=17 MPa. Elastic modulus, E, measures the resistance to deformation of a material when stress is applied. Elastic modulus is defined according to the following equations:

$$E = \frac{\sigma}{e}$$

$$e = \frac{L - L_0}{L_0}$$

wherein e is the strain, σ is the stress, and $L_0$ and L are the length of the polyelectrolyte complex at rest and the length of the polyelectrolyte complex after applying a certain strain, respectively.

In agreement with these Equations the relationship between applied strain and resulting stress in polyelectrolyte complex for e<20 (i.e., percent of elongation less than 2% of length of polyelectrolyte complex at rest) was found to be linear. Further, when the elongation cycle was repeated at a certain ionic strength, $\sigma_{eq}$ was reproducible with minimal hysteresis. This means that the multilayer recovered almost completely when the applied strain is removed (i.e. there was no residual deformation).

Elastic modulus, E, evaluated from the slopes of the stress-strain data as show in FIG. 2, was observed to decrease as the ionic strength increased. That is, the polyelectrolyte complex material becomes softer as more salt is added.

Example 2

Dynamic Storage Modulus of Polyelectrolyte Complexes

The damping behavior of polyelectrolyte complex was tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 10 of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, σ, was recorded.

Figure 3:
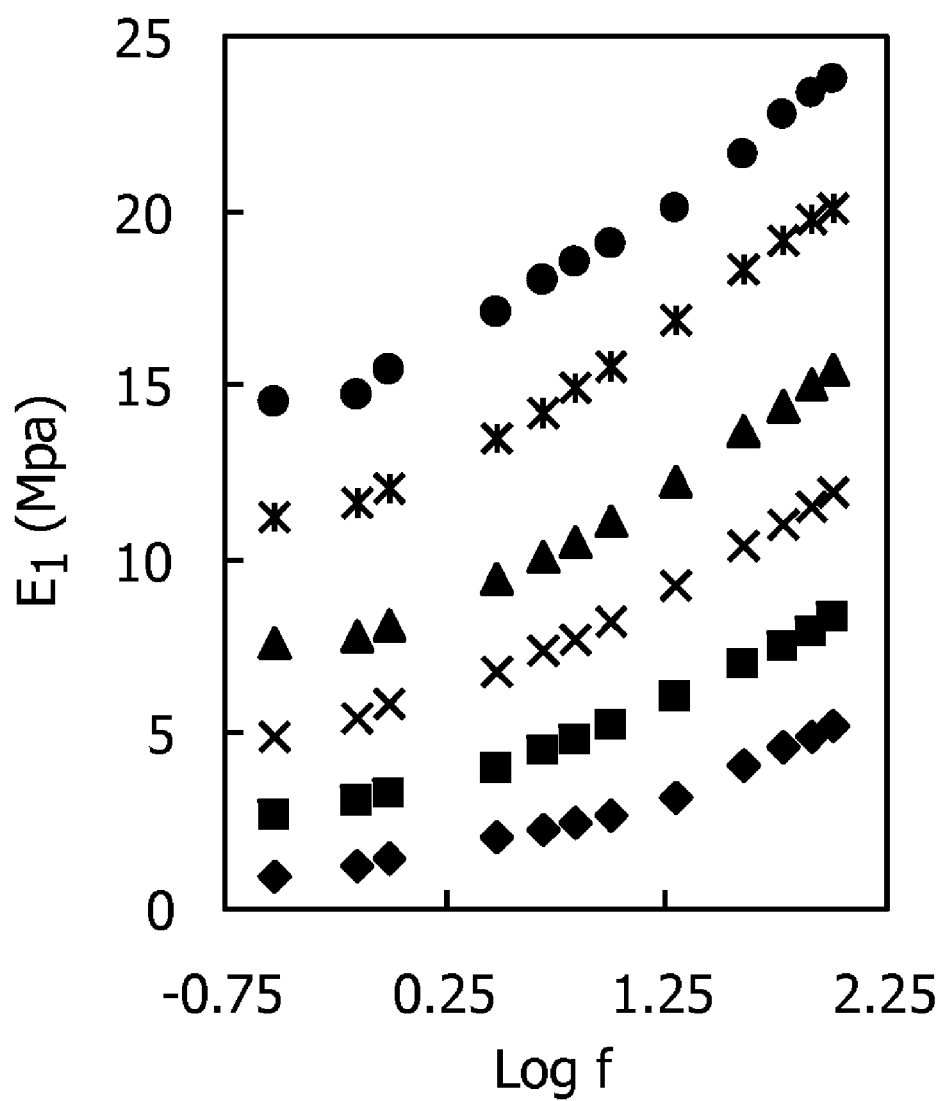
FIG. 3 is a graph showing the Dynamic Storage Modulus behavior of a polyelectrolyte complex after conditioning at several ionic strengths. The data in the graph were obtained according to the method of Example 2.

When a polyelectrolyte complex microcoupon was oscillated sinusoidally (frequency, f=0.1-100 Hz), at constant ionic strength, the relationship between $E_1$ and f showed two distinct regions. See FIG. 3, which shows the dynamic storage modulus behavior of the (PDADMA/PSS)$_{250}$@1.0M NaCl polyelectrolyte complex at different salt concentrations as a function of frequency (Hz). The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction.

At low frequency (0.1-1.0 Hz), the polyelectrolyte complex had enough time to reorient to a new lower free energy state before the next deformation cycle, such that the complex exhibits rubber-like behavior. At high frequency (f>1.0 Hz) or at short time, the polymer chains do not have enough time to relax, such that the complex exhibits glassy behavior.

Example 3

Dynamic Loss Modulus of Polyelectrolyte Complexes

The energy dissipation behavior of polyelectrolyte complex was tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 10 of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, u, was recorded.

Figure 4:
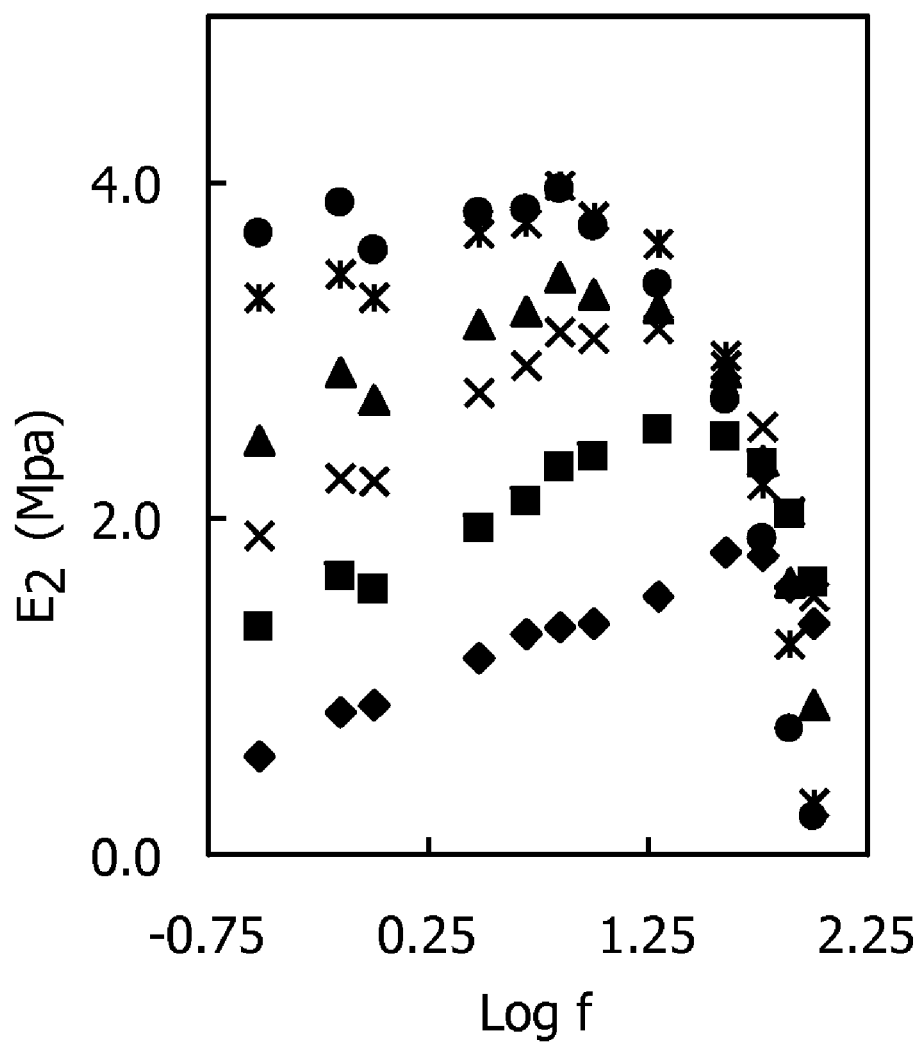
FIG. 4 is a graph showing the Dynamic Loss Modulus behavior of a polyelectrolyte complex after conditioning at several ionic strengths. The data in the graph were obtained according to the method of Example 3.

FIG. 4 depicts the isothermal loss modulus spectra of the polyelectrolyte complex immersed in the salt solutions of various ionic strengths. The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction. According to FIG. 4, $E_2$, was also found to be a function of the rate of the applied strain and the salt concentration of the bathing medium.

In contrast to the low frequency region, where $E_2$ increased with frequency, irrespective of solution ionic strength, the loss modulus deteriorated toward the high frequency end of the spectrum. However, as the salt concentration decreased below 1.0 M, the loss modulus peak broadened progressively. Since $E_2$ is directly proportional to $E_1$ ($E_2=E_1$ Tan Δ), the whole curve shifted towards a lower value of $E_2$ when the ionic strength of the medium increased.

When different systems are compared at the same strain amplitude, $E_2$ serves as a measure of the energy dissipated per cycle. Typically, viscoelastic polymers show $E_2$ values in the range of 0.03-0.05 MPa at 1-10 Hz. At the same frequency range, the polyelectrolyte complex has a loss modulus of 0.5-1.5 MPa and 3.5-4.0 MPa at 1.0 and 0.0 M NaCl respectively. Therefore polyelectrolyte complexes exhibit significant increases in energy dissipation compared to conventional viscoelastic materials.

Example 4

Loss Factor of Polyelectrolyte Complexes

The damping properties of polyelectrolyte complex were tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 10 of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, σ, was recorded.

In dynamic modulus analysis, the strain will be out of phase with the stress (i.e., viscoelastic lag) due to the time necessary for molecular rearrangements. Accordingly, it is possible to probe the extent of damping in polyelectrolyte complexes via the phase angle, Δ.

Figure 5:
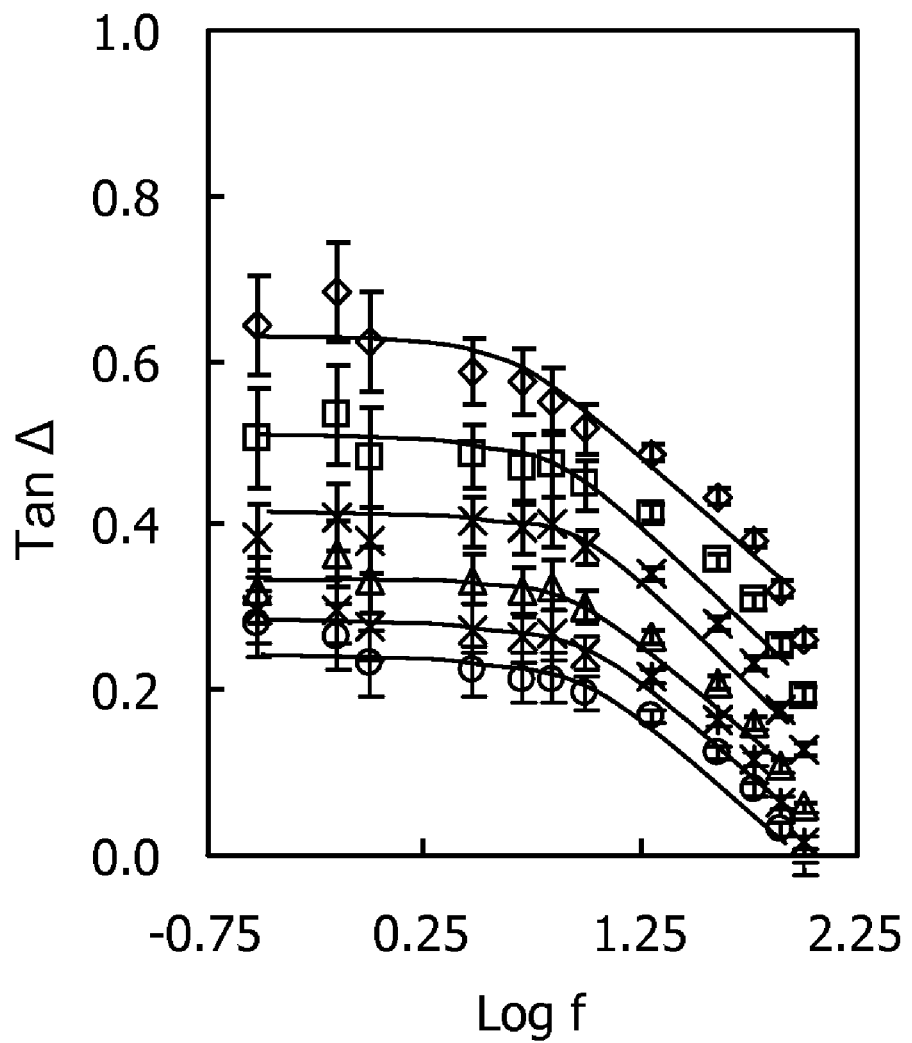
FIG. 5 is a graph showing the damping behavior of a polyelectrolyte complex after conditioning at several ionic strengths. The data in the graph were obtained according to the method of Example 4.

FIG. 5 depicts the damping behavior of polyelectrolyte complex immersed in the salt solutions of various ionic strengths. The curves correspond to salt concentrations as follows: (open circles) 0.0 M NaCl solution; (asterisks) 0.2 M NaCl solution; (open triangles) 0.4 M NaCl solution; (crosses) 0.6 M NaCl solution; (open squares) 0.8 M NaCl solution; (open diamonds) 1.0 M NaCl solution. Solid lines are guides to the eye.

FIG. 5 shows quantitatively that the polyelectrolyte complex was able to dissipate a larger fraction of energy at higher ionic strength. The effect of ionic strength and applied frequency on the damping ability of the multilayer can be summarized as follows: In the low frequency region (0.3-10 Hz), Tan(Δ) remained fairly constant, especially at salt concentrations above 0.2 M. It started to decline at about 20 Hz and progressively deteriorated as the multilayer response became more glassy-like (f>20 Hz). As the salt concentration decreased, damping was observed to diminish.

Compared to other commercially available polymer damping materials such as acrylic adhesives39 (127 μm thick; Tan Δ of 0.38) and rubber adhesives39 (280 μm thick; Tan Δ of 0.25) see Biggerstaff, J. M.; Kosmatka, J. B. J. Compos. Mater. 1999, 33, 1457, Polyelectrolyte complex ((PDADMA/PSS)$_{250}$@1.0M NaCl) at 9.0 μm dry thickness (Tan Δ of 0.62)

showed up to 250% enhancement in damping properties over the range of 0.3-10 Hz. Moreover, the polyelectrolyte complex was much thinner than conventional damping adhesives. Damping on such a small length scale might have utility in MEMS systems.

Example 5

Centrifugal Compaction of Polyelectrolyte Complex Using and Ultracentrifuge

A compacted article comprising polyelectrolyte complex was prepared. Two solutions were prepared, each comprising polyelectrolyte. One solution was prepared by dissolving poly(diallyldimethylammonium chloride) (PDADMAC, 10 wt. %) and sodium chloride (2.5 M) in water. One solution was prepared by dissolved poly(stryrene sulfonate) (PSS, 10 wt. %) and sodium chloride (2.5 M) in water. The solutions were mixed in a beaker and stirred with the aid of a magnetic stir bar. A gelatinous precipitate formed.

The precipitate was allowed to settle and most of the supernatant was poured off. The precipitate was placed in a centrifuge tube, and the tube place in a type TL series 90 Ti rotor. The rotor was placed in a Beckman ultracentrifuge, and the precipitate was centrifuged at 25° C. at 55,000 rpm for 4 hours. An optically transparent solid compact plug of polyelectrolyte complex formed at the bottom of the tube, and the excess liquid was poured off. The plug was removed and cut with a razor blade into shapes for mechanical testing.

Example 6

Modulus of Centrifugally Compacted Polyelectrolyte Complex

Figure 6:
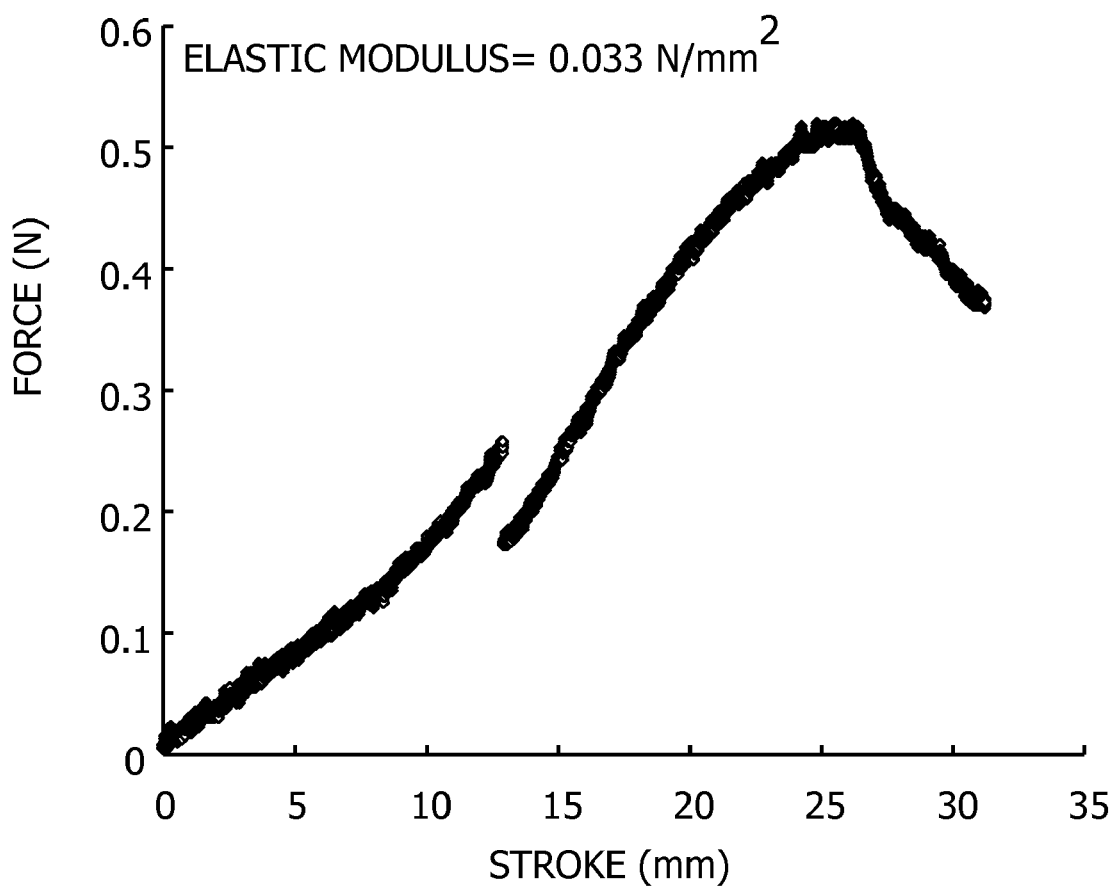
FIG. 6 is a graph showing the Elastic Modulus of a compacted article comprising polyelectrolyte complex formed into a rectangular sheet having millimeter dimensions. The data in the graph were obtained according to the method of Example 6.

The static elastic modulus of the glassy compacted plug comprising PSS/PDADMA prepared according to the method of Example 5 was tested. A sample was cut into flat rectangular sheets of dimension 3 mm×7 mm×26 mm. Each sheet was placed into an Instron mechanical stretching apparatus. The apparatus records the force (Newtons) and the stroke (mm) as the sample is stretched. The sample was not allowed to dry. FIG. 6 depicts a force vs. stroke graph for one sample. The elastic modulus for this particular sample was 0.033 N/mm$^2$ (0.033 MPa). The elastic modulus of five samples was measured and the average modulus was 0.3 N/mm$^2$ (0.3 MPa).

Example 7

Shape Memory

The ability of the glassy compacted plug comprising PSS/PDADMA plug prepared according to the method of Example 5 to remember its shape after deformation was tested. The compacted plug was cut into a rectangular sheet having a length of about 30 mm. The rectangular sheet was stretched using the mechanical apparatus by a further 50 mm so that the new length was 80 mm. The sample was left in the stretched position for 6 minutes and then removed from the apparatus. The sample returned to its original dimensions in about one minute.

Figure 7:
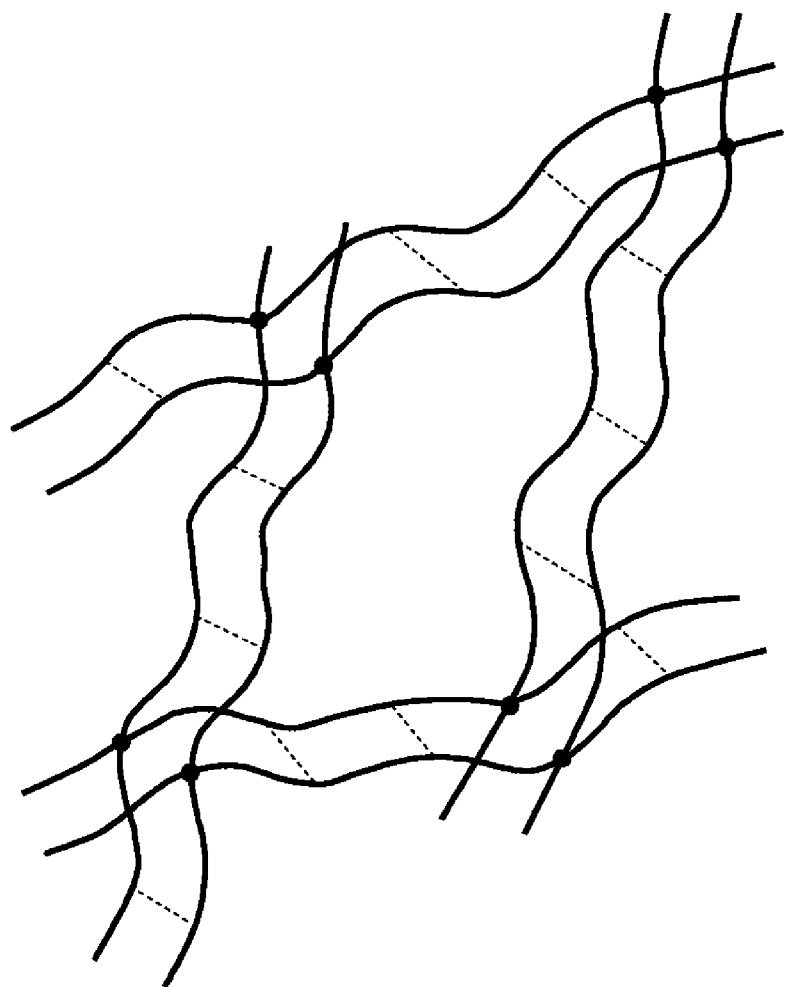
FIG. 7 is a proposed depiction of a polyelectrolyte complex's ladder and network morphology.

Without being held to a particular theory, it is believed that the good damping properties of compacted articles comprising polyelectrolyte complex stem from their unusual internal morphology. It is believed that the crosslinks between positive and negative polymers comprise both "ladder" and "network" character. See FIG. 7 for a depiction of the proposed networked ladder morphology of the polyelectrolyte complex. In FIG. 7, solid lines represent PSS and PDADMA chains. Dashed lines are ladder-type ion pairs. Solid circles represent a network crosslink.

In the absence of salt, all polymers are ion paired and the polyelectrolyte ladders (and individual polymer segments within the ladder complexes) are essentially frozen.

A run of ladder-type ion pairs (as seen in FIG. 7) is like a length of high-mass polymer (the mass is the sum of the two polyelectrolytes involved) that does not interact with its surroundings. Waters of hydration around this run provide opportunities for enhanced molecular motion, further absorbing energy. As ion pairs are broken by the addition of salt, the effective mass of the free runs of paired polyelectrolyte increases, as does the damping effectiveness. The fact that damping is constant over a range of (lower) frequencies is a further advantage of the polyelectrolyte complex system. This behavior is likely due to the statistical distribution of ladder lengths in complexes, with each length of ladder run able to absorb a specific frequency of mechanical energy.

Example 8

Rheometer Studies

The dynamic shear moduli, including the dynamic storage ($G_1$) modulus and the loss ($G_2$) modulus, of the centrifugally compacted article comprising PSS/PDADMA prepared according to the method of Example 5 were tested. The centrifugally compacted PSS/PDADMAC complexes were immersed in solutions of different sodium chloride concentrations (0.0M and 2.5M). The moduli were determined on a controlled stress strain rheometer (Bohlin Gemini, Malvern Instruments) equipped with a parallel plate configuration (diameter=20 mm) in a humidity enclosure chamber. The temperature was controlled to 37.0±0.1° C. using a Peltier plate device. Experimental control and data collection were carried out using a PC-based system and a custom software provided by Bohlin. The samples were first subjected to an oscillation strain sweep at different angular frequencies (1 Hz, 10 Hz, and 30 Hz) to determine the linear viscoelastic domain (LVD). Then, a dynamic angular frequency sweep ($8.10^{-5} \leq f \leq 30$ Hz) was achieved by using a strain value, $\gamma_0$, located for all the frequency range within the LVD.

Example 9

Modulus of PDADMA/PSS Complex

Assuming that the network formed is isotropic with a Poisson ratio of 0.5, E can be obtained from G (using data obtained from Example 8) according to the following:

$$E = 3G.$$

The dynamic storage modulus, $E_1$, and loss modulus, $E_2$, versus frequency were recorded for centrifugally compacted polyelectrolyte complexes doped by contact with an aqueous solution comprising 2.5 M sodium chloride (FIG. 8) and a solution comprising 0.00 M sodium chloride (FIG. 9) using a rheometer.

Figure 8:
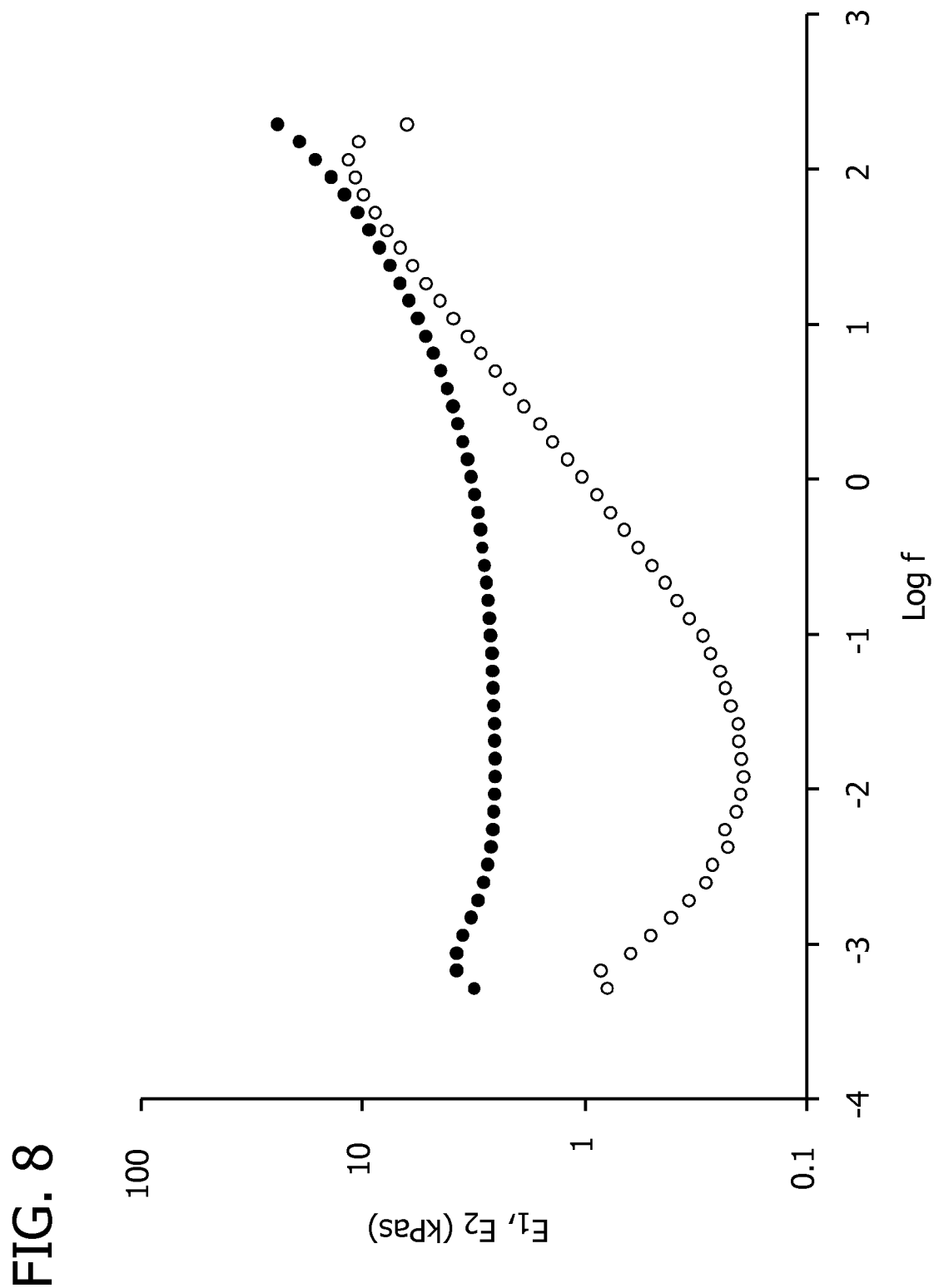
FIG. 8 is a graph showing the dynamic storage modulus, $E_1$, and loss modulus, $E_2$, versus frequency of a compacted article comprising polyelectrolyte complex. The data in the graph were obtained according to the method of Example 9.
Figure 9:
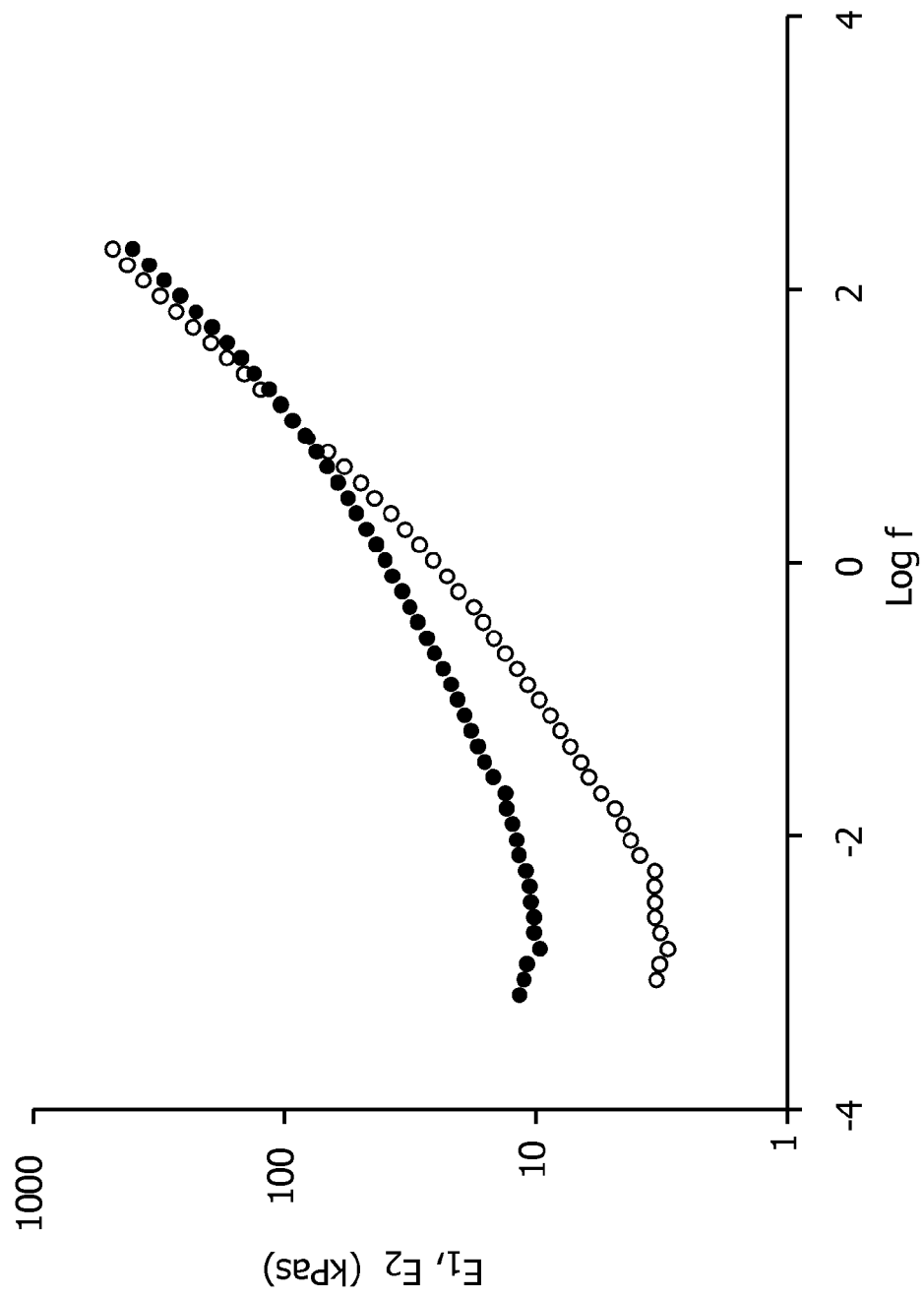
FIG. 9 is a graph showing the dynamic storage modulus, $E_1$, and loss modulus, $E_2$, versus frequency of a compacted article comprising polyelectrolyte complex. The data in the graph were obtained according to the method of Example 9.

In FIGS. 8 and 9, the solid circles represent the dynamic storage modulus data while the open circles represent the loss modulus data.

At low frequencies, the compacted PSS/PDADMAC complexes annealed in water or in 2.50 M NaCl solution exhibited a dominant elastic behavior. $E_1$ has a weak frequency dependence, and it is significantly greater than $E_2$. The plateau value of storage modulus, also called the equilibrium modulus $E_0$, was 3 kPa and 11 kPa for the compacted complexes annealed in 2.50 M and 0.00 M salt, respectively. As previously observed for the polyelectrolyte multilayers, the mechanical properties of the complexes depend on the ionic strength of the solution in which they are immersed. As the salt concentration of the annealing solution (and so in the complexes) increases, the compacted polyelectrolyte complexes are softer (decrease of $E_0$ values).

Figure 10:
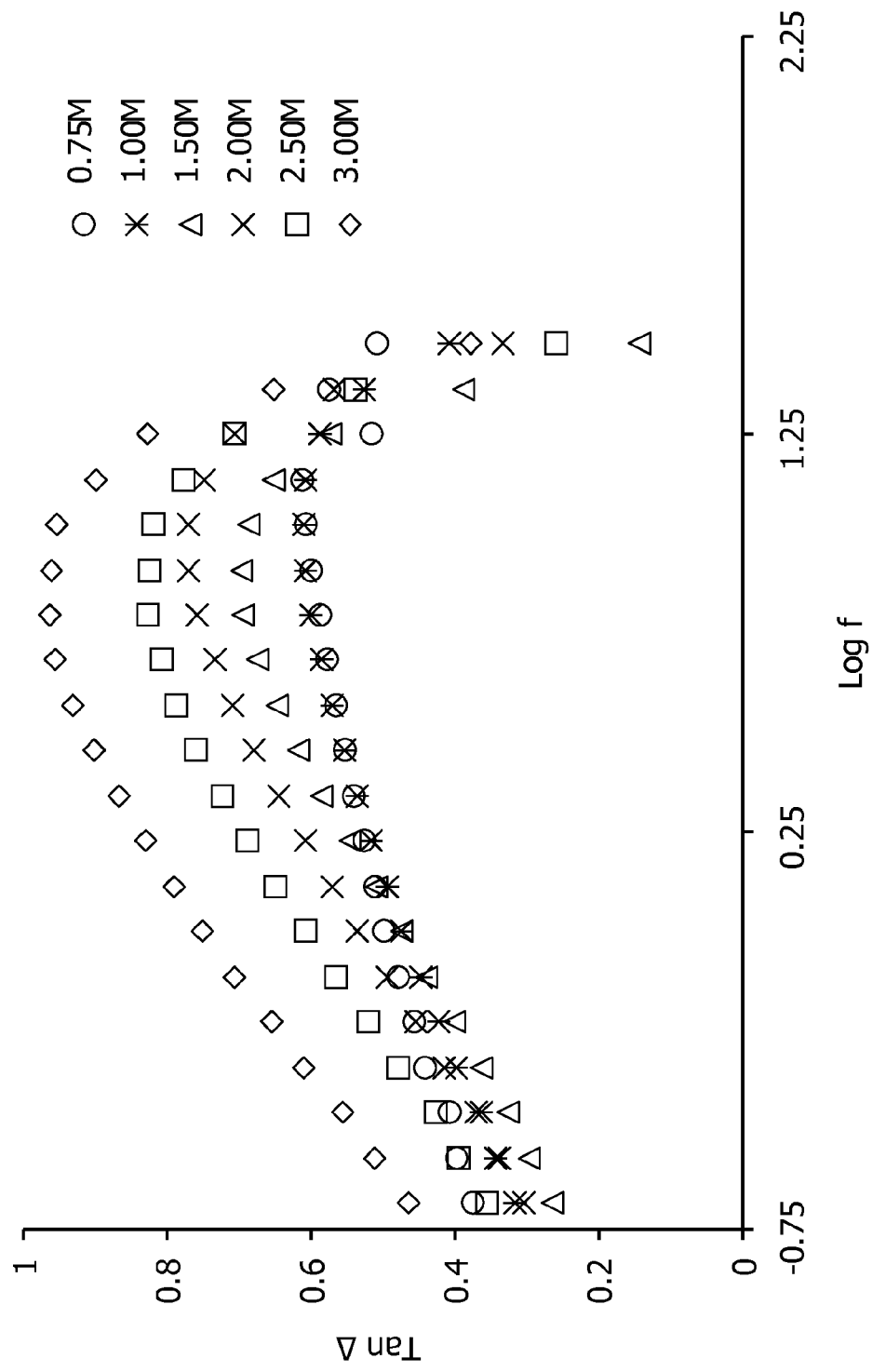
FIG. 10 is a graph showing the damping behavior of a polyelectrolyte complex after conditioning at several ionic strengths. The data in the graph were obtained according to the method of Example 9.

The damping properties of the centrifugally compacted PSS/PDADMAC complexes are similar to those observed in the noncompacted polyelectrolyte complex (Example 4). $\Delta$ varies between 16° and 50°. Moreover, between 0.3-30 Hz, Tan($\Delta$) exhibits not only the same trend observed for the noncompacted polyelectrolyte complexes but also these values lie in the same range. See FIG. 10, which is a graph depicting the damping ability versus frequency at 37° C. In FIG. 10, the curves correspond to salt concentrations as follows: (open circles) 0.75 M NaCl solution; (asterisks) 1.00 M NaCl solution; (open triangles) 1.5 M NaCl solution; (crosses) 2.0 M NaCl solution; (open squares) 2.5 M NaCl solution; (open diamonds) 3.0 M NaCl solution. Solid lines are guides to the eye. The damping ability of the compacted polyelectrolyte complexes is improved as the salt concentration increases.

Compacted PSS/PDADMAC complexes having moduli in the kPa range are of widespread interest since many native tissues have moduli in this range. For example in the human intervertebral disks, the nucleus pulposus (~1 kPa) (Iatridis, J. C.; Setton, L. A.; Weidenbaum, M.; Mow, V. C. J. Biomechanics 1997, 30, 1005) and the annulus fibrosis (~100 kPa) (Iatridis, J. C.; Kumar, S.; Foster, R. J.; Weidenbaum, M.; Mow, V. C. J. Ortho. Res. 1999, 17, 732) have moduli in this range.

Example 10

Reforming a Polyelectrolyte Complex Article by Embossing a Doped Polyelectrolyte Complex Article A sample of PSS/PDADMA polyelectrolyte complex was centrifugally compacted as in Example 5. A piece of complex about 1 mm thick and 20 mm diameter was sliced off this sample with a razor blade. The sliced sample was doped to a doping level of approximately 0.8 by placing it in contact with a solution of 2.5 M NaCl at room temperature for 30 minutes. A microfluidic channel pattern engraved into a glass slide was then placed over the polyelectrolyte complex slice, with the channel pattern in contact with the wet (fully hydrated) slice of PSS/PDADMA. The channel pattern comprised a plurality of linear, parallel features 1 mm apart, of width 230 micrometers and depth 97 micrometers. A pressure of 1.5 psi was applied with a weight for 15 hours at room temperature, pressing the pattern into the PSS/PSDADMA slice. When the glass slide was removed, the surface of the PSS/PDADMA slice had been embossed with the microfluidic channel pattern on the glass slide. The PSS/PDADMA slice was then exposed to 1.0 M NaCl to decrease the doping level to about 0.45. Further microscopic examination, along with measurement of the profile with a profilometer, revealed that the detailed features of the pattern had been faithfully reproduced on the surface of the PSS/PDAMDA slice. This pattern was persistent.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A method for modifying a complex shear modulus of an article comprising a polyelectrolyte complex, the polyelectrolyte complex being an intermolecular blend of a predominantly positively-charged polyelectrolyte polymer and a predominantly negatively charged polyelectrolyte polymer and containing at least about 20 wt. % water, the method comprising:

contacting the article with a first solution to increase the doping level ratio in the polyelectrolyte complex from a first salt doping level ratio to a second doping level ratio, whereby increasing the doping level ratio in the polyelectrolyte complex decreases the complex shear modulus of the polyelectrolyte complex from a first complex shear modulus to a second complex shear modulus;

applying a mechanical force to compact the polyelectrolyte complex into a persistent shape at the second complex shear modulus;

contacting the compacted polyelectrolyte complex with a second solution to change the doping level ratio in the polyelectrolyte complex from the second doping level ratio to a third doping level ratio, whereby changing the doping level ratio in the polyelectrolyte complex changes the complex shear modulus of the polyelectrolyte complex from the second complex shear modulus to a third complex shear modulus.

2. The method of claim 1 wherein said mechanical force is applied by a mechanism selected from the group consisting of piston, syringe, screw, rollers, hydrostatic pressure, magnetic field, and any combination thereof.

3. The method of claim 1 wherein the complex shear modulus is between about 1 kPa to about 300 MPa at a frequency between about 0.1 Hz and about 10,000 Hz.

4. The method of claim 1 wherein the compacted article has a loss factor of at least about 0.2 at a frequency between about 0.1 Hz and about 10,000 Hz, or at least about 0.25 at a frequency between about 0.1 Hz and about 10,000 Hz.

5. The method of claim 1 wherein the polyelectrolyte complex has a loss factor of at least about 0.2 at a frequency of about 10 Hz.

6. The method of claim 1 wherein the salt in the first solution comprises a cation selected from the group consisting of alkali metal cations, alkaline earth metal cations, transition metal cations, semi-metallic cations, amine cations, and combinations thereof.

7. The method of claim 1 wherein the salt in the first solution comprises an anion selected from the group consisting of halide anions, oxoanions, carboxylate anions, and combinations thereof.

8. The method of claim 1 wherein the salt in the first solution is selected from the group consisting of sodium chloride, potassium chloride, magnesium chloride, calcium chloride, aluminum chloride, trisodium citrate, disodium hydrogencitrate, sodium dihydrogencitrate, tripotassium citrate, dipotassium hydrogencitrate, potassium dihydrogencitrate, magnesium citrate, calcium citrate, trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, magnesium phosphate, and combinations thereof.

9. The method of claim 1 wherein the polyelectrolyte complex further comprises an additive selected from the group consisting of metallic oxide particles, magnetic particles, needle-like clay minerals, carbon-based fibers, and combinations thereof.

10. The method of claim 1 wherein the polyelectrolyte complex further comprises an antibacterial agent and/or an anti-inflammation agent and/or antirejection agent and/or a growth factor.

11. The method of claim 1 wherein the first solution comprises calcium cations and the second solution comprises sodium cations.

12. The method of claim 1 wherein contacting the article with the second solution decreases the doping level ratio of the polyelectrolyte complex thereby resulting in the third complex shear modulus being greater than the second complex shear modulus.

13. The method of claim 1 wherein the polyelectrolyte complex comprises an interior region and a surface stratum, the interior region comprises an interior positively charged polyelectrolyte polymer and an interior negatively charged polyelectrolyte polymer, the surface stratum comprises a surface positively charged polyelectrolyte polymer and a surface negatively charged polyelectrolyte polymer, and either or both of the surface positively charged polyelectrolyte polymer and the surface negatively charged polyelectrolyte polymer differ from the interior positively charged polyelectrolyte polymer and the interior negatively charged polyelectrolyte polymer.

14. The method of claim 13 wherein the surface stratum and the interior region each have a complex shear modulus and the complex shear modulus of the surface stratum is greater than the complex shear modulus of the interior region.

15. The method of claim 14 wherein the complex shear modulus of the surface stratum is at least 2 times greater than the complex shear modulus of the interior region.

\* \* \* \* \*